(12) United States Patent
Ichiki et al.

(10) Patent No.: US 10,295,454 B2
(45) Date of Patent: May 21, 2019

(54) MICROPARTICLE DETECTION SYSTEM AND MICROPARTICLE DETECTION PROGRAM

(71) Applicants: The University of Tokyo, Tokyo (JP); NIKON CORPORATION, Tokyo (JP)

(72) Inventors: Takanori Ichiki, Tokyo (JP); Kuno Suzuki, Iruma-gun (JP); Daishi Tanaka, Konosu (JP)

(73) Assignee: THE UNIVERSITY OF TOKYO NIKON CORPORATION (JP)

( * ) Notice: Subject to any disclaimer, the term of this patent is extended or adjusted under 35 U.S.C. 154(b) by 0 days.

(21) Appl. No.: 15/786,450

(22) Filed: Oct. 17, 2017

(65) Prior Publication Data

US 2018/0100793 A1   Apr. 12, 2018

Related U.S. Application Data

(63) Continuation of application No. PCT/JP2016/062591, filed on Apr. 21, 2016.

(30) Foreign Application Priority Data

Apr. 21, 2015 (JP) .................................. 2015-087021

(51) Int. Cl.
*G01N 15/00* (2006.01)
*G01N 15/02* (2006.01)
(Continued)

(52) U.S. Cl.
CPC ............. *G01N 15/14* (2013.01); *G01N 15/02* (2013.01); *G01N 15/0227* (2013.01);
(Continued)

(58) Field of Classification Search
None
See application file for complete search history.

(56) References Cited

U.S. PATENT DOCUMENTS

2009/0238413 A1   9/2009   Ikeda et al.
2012/0264948 A1*  10/2012  Hilbert ................. B01D 61/025
                                                         548/495
(Continued)

FOREIGN PATENT DOCUMENTS

EP   1 297 336 B1   3/2005
EP   2 889 623 A1   7/2015
(Continued)

OTHER PUBLICATIONS

International Search Report and Written Opinion dated Jun. 28, 2016, in International Patent Application No. PCT/JP2016/062591, 13 pages.

*Primary Examiner* — Shawn Decenzo
(74) *Attorney, Agent, or Firm* — Squire Patton Boggs (US) LLP

(57) ABSTRACT

A microparticle detection system includes a stage unit including a mounting surface on which a fluid device having a flow path through which a sample containing microparticles is movable is capable of being mounted, an emission unit configured to emit illumination light to the flow path, an imaging unit configured to image scattered light generated from microparticles in the sample when illumination light is emitted, an identification unit configured to identify the microparticles included in the image for each of the microparticles on the basis of the image captured by the imaging unit, a particle size determination unit configured to determine a particle size of the microparticle for each of the microparticles identified by the identification unit, a zeta potential determination unit configured to determine a zeta potential of the microparticle for each of the microparticles identified by the identification unit, and a correlation unit configured to associate the particle size for each of the microparticles determined by the particle size determination (Continued)

unit with the zeta potential for each of the microparticles determined by the zeta potential determination unit for each of the microparticles.

21 Claims, 22 Drawing Sheets

(51) Int. Cl.
*G01N 15/10* (2006.01)
*G01N 15/14* (2006.01)
*G01N 27/26* (2006.01)
*G01N 33/53* (2006.01)

(52) U.S. Cl.
CPC ..... *G01N 15/1429* (2013.01); *G01N 15/1484* (2013.01); *G01N 27/26* (2013.01); *G01N 33/53* (2013.01); *G01N 2015/0053* (2013.01); *G01N 2015/1006* (2013.01); *G01N 2015/1075* (2013.01); *G01N 2015/1486* (2013.01); *G01N 2015/1493* (2013.01)

(56) References Cited

U.S. PATENT DOCUMENTS

| | | | |
|---|---|---|---|
| 2015/0168400 A1* | 6/2015 | Ichiki | G01N 33/57484 |
| | | | 204/450 |
| 2016/0256559 A1* | 9/2016 | Onyuksel | A61K 47/60 |
| 2016/0320289 A1* | 11/2016 | Tanaka | G01N 15/00 |
| 2016/0338970 A1* | 11/2016 | Farokhzad | A61K 9/0019 |
| 2017/0074768 A1* | 3/2017 | Moitzi | G01N 15/0227 |
| 2017/0219477 A1* | 8/2017 | Ichiki | B01L 3/502715 |
| 2018/0147166 A1* | 5/2018 | Dong | A61K 9/127 |

FOREIGN PATENT DOCUMENTS

| | | |
|---|---|---|
| JP | 2004-503779 A | 2/2004 |
| JP | 2006-276000 A | 10/2006 |
| JP | 2007-322329 A | 12/2007 |
| JP | 2009-229103 A | 10/2009 |
| WO | WO 2014/030590 A1 | 2/2014 |

* cited by examiner

|  |  | t0 | t1 | t2 | ... | t48 | t49 | t50 |
|---|---|---|---|---|---|---|---|---|
| P1 | X | x10 | x11 | x12 | ... | x148 | x149 | x150 |
|    | Y | y10 | y11 | y12 | ... | y148 | y149 | y150 |
| P2 | X | x20 | x21 | x22 | ... | x248 | x249 | x250 |
|    | Y | y20 | y21 | y22 | ... | y248 | y249 | y250 |
| ... |  | ... | ... | ... | ... | ... | ... | ... |
| Pn | X | xn0 | xn1 | xn2 | ... | xn48 | xn49 | xn50 |
|    | Y | yn0 | yn1 | yn2 | ... | yn48 | yn49 | yn50 |

| PARTICLE NUMBER | PARTICLE CORRELATION INFORMATION |
|---|---|
| P1 | PC1(d1, $\xi 1$) |
| P2 | PC2(d2, $\xi 2$) |
| ... | ... |
| Pn | PCn(dn, $\xi n$) |

|  | BEFORE ANTIBODY ACTS ○ | | AFTER ANTIBODY ACTS ● | | RATE OF CHANGE (%) |
|---|---|---|---|---|---|
|  | COUNT | PROPORTION (%) | COUNT | PROPORTION (%) |  |
| DM1 | 24 | 28 | 13 | 29 | 3.5 |
| DM2 | 28 | 31 | 0 | 0 | >−100 |
| DM3 | 16 | 19 | 6 | 13 | −32 |
| DM4 | 19 | 22 | 26 | 58 | 163 |

FIG. 22

| FLOW PATH NUMBER | ANTIBODY ADDED | ANTIGEN | DETERMINATION EXAMPLE 1 | DETERMINATION EXAMPLE 2 | DETERMINATION EXAMPLE 3 | DETERMINATION EXAMPLE 4 |
|---|---|---|---|---|---|---|
| FIRST FLOW PATH | ANTI-CD9 ANTIBODY | EXOSOME MEMBRANE PROTEIN | POSITIVE | POSITIVE | POSITIVE | NEGATIVE |
| SECOND FLOW PATH | ANTI-CD81 ANTIBODY | EXOSOME MEMBRANE PROTEIN | POSITIVE | POSITIVE | NEGATIVE | NEGATIVE |
| THIRD FLOW PATH | ANTI-HER2 ANTIBODY | BREAST CANCER MARKER | NEGATIVE | POSITIVE | POSITIVE | NEGATIVE |
| FOURTH FLOW PATH | ANTI-CD147 ANTIBODY | COLORECTAL CANCER MARKER | NEGATIVE | POSITIVE | NEGATIVE | POSITIVE |

FIG. 23

| | DIAGNOSIS | INSTRUCTION EXAMPLE |
|---|---|---|
| DETERMINATION EXAMPLE 1 | NO BREAST CANCER OR COLORECTAL CANCER | HEALTHY |
| DETERMINATION EXAMPLE 2 | BREAST CANCER AND COLORECTAL CANCER ARE STRONGLY SUSPECTED | EXAMINE CONFIRMATORY DIAGNOSTIC TEST SUCH AS IMAGE DIAGNOSIS AND CYTODIAGNOSIS |
| DETERMINATION EXAMPLE 3 | BREAST CANCER IS STRONGLY SUSPECTED | EXAMINE CONFIRMATORY DIAGNOSTIC TEST SUCH AS IMAGE DIAGNOSIS AND CYTODIAGNOSIS |
| DETERMINATION EXAMPLE 4 | THERE IS A POSSIBILITY OF COLORECTAL CANCER | EXAMINE CONFIRMATORY DIAGNOSTIC TEST TOGETHER WITH THE RESULT OF STOOL ANALYSIS |

FIG. 26

|  | COUNT | | POSITIVITY (%) | DETERMINATION |
|---|---|---|---|---|
|  | IN GATE AREA G | OUTSIDE GATE AREA G | | |
| PRODUCTION LOT 1 | 1000 | 10 | 99.1 | SUITABLE |
| PRODUCTION LOT 2 | 500 | 500 | 50.0 | UNSUITABLE |
| PRODUCTION LOT 3 | 900 | 100 | 90.0 | UNSUITABLE |
| PRODUCTION LOT 4 | 100 | 5 | 95.2 | SUITABLE |

# MICROPARTICLE DETECTION SYSTEM AND MICROPARTICLE DETECTION PROGRAM

Priority is claimed on Japanese Patent Application No. 2015-087021 filed Apr. 21, 2015. This is a continuation application of PCT/JP2016/062591 filed Apr. 21, 2016, the content of which is incorporated herein by reference.

BACKGROUND

Field of the Invention

The present invention relates to a microparticle detection system and a microparticle detection program.

Background

For example, a device configured to image microparticles that move in a medium through microscopic observation under dark field illumination, process the captured image, and thereby measure the number of microparticles and a movement speed thereof is known, as in Japanese Unexamined Patent Application, First Publication No. 2009-229103. In such a device, on the basis of a plurality of images captured at different timings, the number of microparticles and a movement speed thereof are measured by tracking movement trajectories of the microparticles.

SUMMARY

However, in the above-described technology of the related art, it is not possible to determine a correlation between a zeta potential of a plurality of microparticles present in a medium and a microparticle size.

The present invention provides a microparticle detection system and a microparticle detection program through which it is possible to determine a correlation between a zeta potential of microparticles such as the extracellular endoplasmic reticulum present in a medium and a microparticle size.

[1] An aspect of the present invention is a microparticle detection system including: a stage unit including a mounting surface on which a fluid device having a flow path through which a sample containing microparticles is movable is capable of being mounted, a particle size determination unit configured to determine a particle size of the microparticles that move in the flow path, a zeta potential determination unit configured to determine a zeta potential of the microparticles that move in the flow path, and a correlation unit configured to associate the particle size with the zeta potential of the microparticle for each of the microparticles.

[2] An aspect of the present invention is a microparticle detection program causing a computer including a stage unit having a mounting surface on which a fluid device including a flow path through which a sample containing microparticles is movable is capable of being mounted to execute: a particle size determination step of determining a particle size of the microparticles that move in the flow path, a zeta potential determination step of determining a zeta potential of the microparticles that move in the flow path, and a correlation step of associating the particle size with the zeta potential of the microparticle for each of the microparticles.

[3] An aspect of the present invention is a microparticle detection system including a stage unit including a mounting surface on which a fluid device having a flow path through which a sample containing microparticles is movable is capable of being mounted, an emission unit configured to emit illumination light to the flow path along an optical axis that is orthogonal to the mounting surface and parallel to a first direction intersecting a plane parallel to the flow path, an adjustment unit configured to converge the illumination light so that a width of the illumination light in a second direction orthogonal to the first direction becomes a minimum inside the flow path and an emission area at a position on a side surface on an emission light incident side of the flow path is confined within the side surface, an imaging unit configured to image scattered light generated when the illumination light is emitted, an identification unit configured to identify the microparticles included in the image for each of the microparticles on the basis of the image captured by the imaging unit, a particle size determination unit configured to determine a particle size of the microparticle for each of the microparticles identified by the identification unit, a zeta potential determination unit configured to determine a zeta potential of the microparticle for each of the microparticles identified by the identification unit, and a correlation unit configured to associate the particle size for each of the microparticles determined by the particle size determination unit with the zeta potential for each of the microparticles determined by the zeta potential determination unit for each of the microparticles.

BRIEF DESCRIPTION OF THE DRAWINGS

FIG. 12 is a diagram showing an example of a particle list stored in a storage unit according to the present embodiment.

FIG. 13 is a diagram showing an example of a particle correlation list stored in the storage unit according to the present embodiment.

FIG. 22 is a table showing an example of a disease determination panel of the present embodiment.

FIG. 23 is a table showing an example of diagnosis and an instruction panel of diseases of the present embodiment.

FIG. 26 is a diagram showing an example of evaluation performed by the evaluation unit of the present embodiment.

DESCRIPTION OF EMBODIMENTS

A particle detection system 1 of the present embodiment includes a particle detection device 100 and a control device 5. Note that, in the following description, when particles detected by the particle detection system 1 are extracellular endoplasmic reticulum, the particle detection system 1 will be referred to as an extracellular endoplasmic reticulum detection system. First, the particle detection device 100 will be described with reference to FIG. 1 to FIG. 10.

[Configuration of Particle Detection Device]

Figure 1:
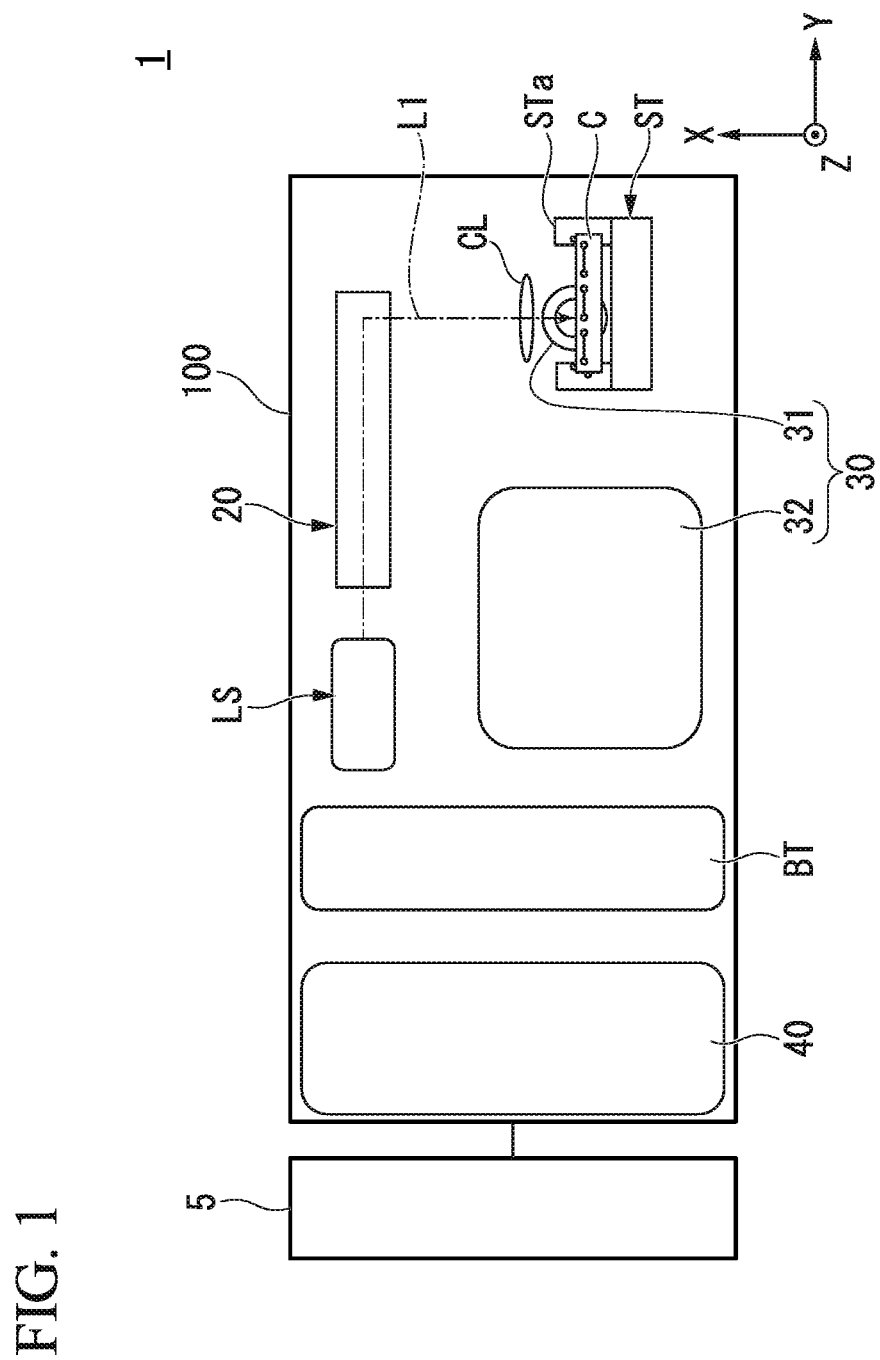
FIG. 1 is a schematic plan view of a particle detection system according to the present embodiment.
Figure 2:
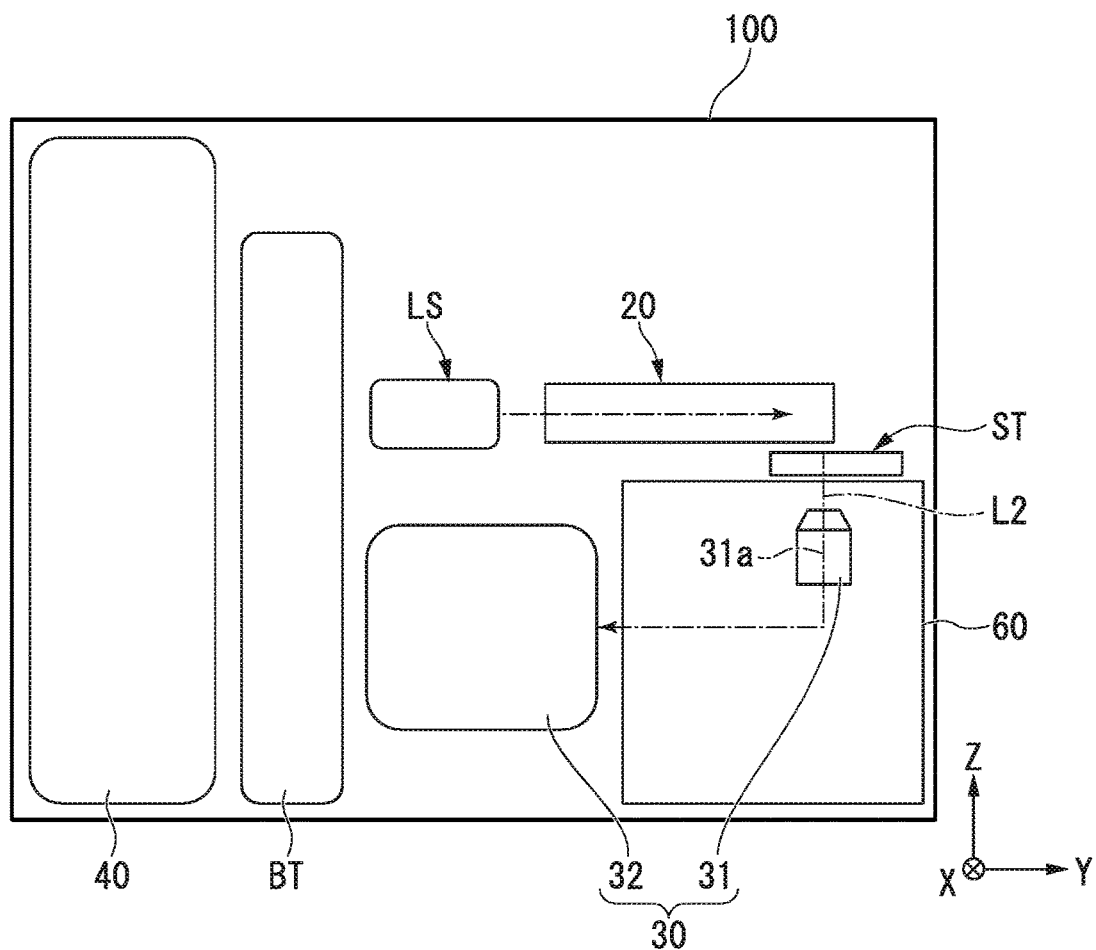
FIG. 2 is a schematic front view of a particle detection device according to the present embodiment.

FIG. 1 is a schematic plan view of the particle detection system 1 according to an embodiment. FIG. 2 is a schematic front view of the particle detection device 100 according to the embodiment.

The particle detection device 100 emits illumination light L1 to a fluid device C with the fluid device C as a detection target, observes scattered light L2 from the fluid device C, and thus detects information about particles in the fluid device C. The particle detection device 100 includes a light source unit LS, an emission unit 20, an adjustment unit CL, a stage unit ST, a detection unit 30, a transmission unit 40, and the control device 5. The particle detection device 100 and the fluid device C constitute the particle detection system 1.

In the following description, a direction that is orthogonal to a mounting surface STa of the stage unit ST and is orthogonal to a surface (not shown) parallel to the illumination light L1 is defined as an x direction (x axis; third direction), a direction that is parallel to the mounting surface STa and is orthogonal to the x direction is defined as a y direction (y axis), and a vertical direction that is orthogonal to the x direction and the y direction is defined as a z direction (z axis; second direction).

First, the fluid device C, which is a detection target, will be described.

The fluid device C in the present embodiment is, for example, an electrophoresis analysis chip used for analyzing a specimen. Examples of microparticle specimens include cells, bacteria, viruses, extracellular endoplasmic reticulum (extracellular vesicles), synthetic polymers, inorganic substances, microparticles including a metal as a base material, magnetic microparticles, and microparticles having a polymer micelle structure. Examples of microparticles including a synthetic polymer as a base material include polystyrene latex particles. Examples of microparticles including an inorganic substance as a base material include silica particles. Examples of microparticles including a metal as a base material include iron beads. Examples of magnetic microparticles include magnetic beads containing iron, iron oxide, nickel, or the like. Both microparticles including a synthetic polymer, an inorganic substance, or a metal as a base material and magnetic microparticles may include particles whose surfaces are modified with peptides, proteins, cells, various compounds, or the like.

In the present embodiment, a case in which an extracellular endoplasmic reticulum analysis chip for analyzing the extracellular endoplasmic reticulum is used as an electrophoresis analysis chip will be described. In this specification, the extracellular endoplasmic reticulum refers to a lipid vesicle including exosomes, apoptotic substances, microvesicles, and the like. The size of the extracellular endoplasmic reticulum is about 30 nm to 1 μm in diameter. The extracellular endoplasmic reticulum is a cell secretion and has a surface on which a protein derived from a secretion source cell is expressed.

The extracellular endoplasmic reticulum analysis chip (electrophoresis analysis chip) according to the present embodiment will be described below using a case in which an exosome is analyzed as an example.

[Exosome]

An exosome is a lipid vesicle with a diameter of about 30 to 200 nm and is secreted into a body fluid such as blood, urine, saliva from various cells such as tumor cells, dendritic cells, T cells, and B cells as a fused substance of an endosome and a cell membrane.

Abnormal cells such as cancer cells present in a living body express proteins specific to cell membranes thereof. An exosome is a cell secretion and has a surface on which a protein derived from a secretion source cell is expressed.

Thus, when the protein expressed on the surface of an exosome is analyzed, it is possible to detect an abnormality of a secretion source cell. Here, the surface of the exosome is a membrane surface of a lipid vesicle secreted from the cell and is a part in which the secreted exosome comes in contact with an environment in a living body.

Since an exosome may be detected in blood that circulates in a living body, when the exosome is analyzed, it is possible to detect an abnormality in the living body without performing a biopsy test.

[Analysis of Exosome]

For example, analysis of an exosome using an extracellular endoplasmic reticulum analysis chip can be performed as follows. First, a detection target exosome is purified. Next, the exosome is brought into contact with a specific binding substance. Here, the specific binding substance refers to a substance that can specifically bind to molecules present on the surface of the exosome, and details thereof will be described below. Next, a zeta potential of the exosome is measured using an extracellular endoplasmic reticulum analysis chip, and analysis is performed. This analysis can be applied for not only an exosome, but also can be used widely for general analysis of the extracellular endoplasmic reticulum.

(Specific Binding Substance)

As the specific binding substance, for example, an antibody, a modified antibody, an aptamer, a ligand molecule, and the like may be exemplified. As an antibody, IgG IgA, IgD, IgE, IgM, and the like may be exemplified. As IgG, IgG1, IgG2, IgG3, IgG4, and the like may be exemplified. As IgA, IgA1, IgA2, and the like may be exemplified. As IgM, IgM1, IgM2, and the like may be exemplified. As a modified antibody, Fab, F(ab')2, scFv, and the like may be exemplified. As an aptamer, a peptide aptamer, a nucleic acid aptamer, and the like may be exemplified. As a ligand molecule, a ligand of a receptor protein when a detection target molecule present on the surface of an exosome is the receptor protein and the like may be exemplified. For example, when the molecule present on the surface of an exosome is an interleukin, G proteins may be exemplified as the ligand molecules.

In addition, a specific binding substance may be labeled with a labeling substance. Examples of the labeling substance include biotin, avidin, streptavidin, neutravidin, glutathione-S-transferase, glutathione, fluorescent dyes, polyethylene glycol, and charged molecules such as mellitic acid.

(Purification of Exosome)

Processes of this analysis will be described. First, an exosome is purified from a sample containing exosomes. As the sample, blood, urine, breast milk, a bronchoalveolar lavage fluid, an amniotic fluid, a malignant exudate, saliva, or a cell culture medium may be exemplified according to the purpose. Among these, an exosome is easily purified from blood and urine.

As a method of purifying an exosome, ultracentrifugation, ultrafiltration, continuous flow electrophoresis, chromatography, a method using a g-TAS (Micro-Total Analysis Systems) device, and the like may be exemplified.

(Reaction Between Exosome and Specific Binding Substance)

Next, the exosome is brought into contact with a specific binding substance (such as an antibody and an aptamer). When detection target molecules are present on the surface of the exosome, a specific binding substance-exosome complex is formed. When the specific binding substance is appropriately selected, it is possible to detect an abnormality related to diseases, for example, cancer, obesity, diabetes, and neurodegenerative diseases. In addition, it is possible to evaluate an exosome whose functions are modified, for example, using a specific binding substance that specifically binds to a peptide or a protein for an exosome that causes the peptide or the protein to be artificially expressed on the membrane surface.

(Measurement of Zeta Potential)

As an example, a case in which an antibody is used as a specific binding substance will be described. After the exosome and an antibody react, a zeta potential of the exosome having been reacted with the antibody is measured. The zeta potential is a surface charge of microparticles in a solution. For example, while the exosome is charged negatively, the antibody is charged positively. Therefore, a zeta potential of an antibody-exosome complex is shifted positively compared to a zeta potential of the exosome alone. Thus, when the zeta potential of the exosome having been reacted with an antibody is measured, it is possible to detect expression of antigens on the membrane surface of the exosome. This similarly applies to not only an antibody but also a specific binding substance charged positively.

For example, the exosome may be electrophoresed in a microflow path of an extracellular endoplasmic reticulum analysis chip, an electrophoretic speed S of the exosomes may be optically measured, and a zeta potential of the exosome can be calculated using the Smoluchowski equation shown in the following Formula. 1 on the basis of the measured electrophoretic speed S of the exosomes.

[Math. 1]

$$U = \left(\frac{\varepsilon}{\eta}\right)\zeta \quad (1)$$

In Formula (1), U denotes an electrophoretic mobility of a measurement target exosome, and ε and η denote a dielectric constant and a viscosity coefficient of a sample solution, respectively. In addition, the electrophoretic mobility U can be calculated by dividing the electrophoretic speed S by an electric field strength in the micro flow path.

The electrophoretic speed S of the exosomes can be measured, for example, when the exosome is electrophoresed in a micro flow path of an extracellular endoplasmic reticulum analysis chip, for example, a laser beam is emitted to the exosomes that flow in the micro flow path, and a particle image according to Rayleigh scattered light is acquired. As the laser beam, for example, a laser beam with a wavelength of 405 nm and an intensity of 150 mW may be exemplified.

(Measurement of Particle Size)

For example, the exosomes may be electrophoresed in a micro flow path of an extracellular endoplasmic reticulum analysis chip, the electrophoretic speed S of the exosomes may be optically measured, and a particle size d of the exosomes can be calculated using the Stokes-Einstein equation shown in the following Formula (2) on the basis of the measured electrophoretic speed S of the exosomes.

[Math. 2]

$$d = \frac{kT}{3\pi\eta D} \quad (2)$$

In Formula (2), d denotes a particle size of an exosome, k denotes the Boltzmann constant, T denotes an absolute temperature, η denotes a viscosity coefficient of a sample solution, and D denotes a diffusion coefficient of microparticles. That is, the particle size d of an exosome can be calculated on the basis of a state of the Brownian motion of a measurement target exosome.

[Basic Structure of Extracellular Endoplasmic Reticulum Analysis Chip]

Figure 3:
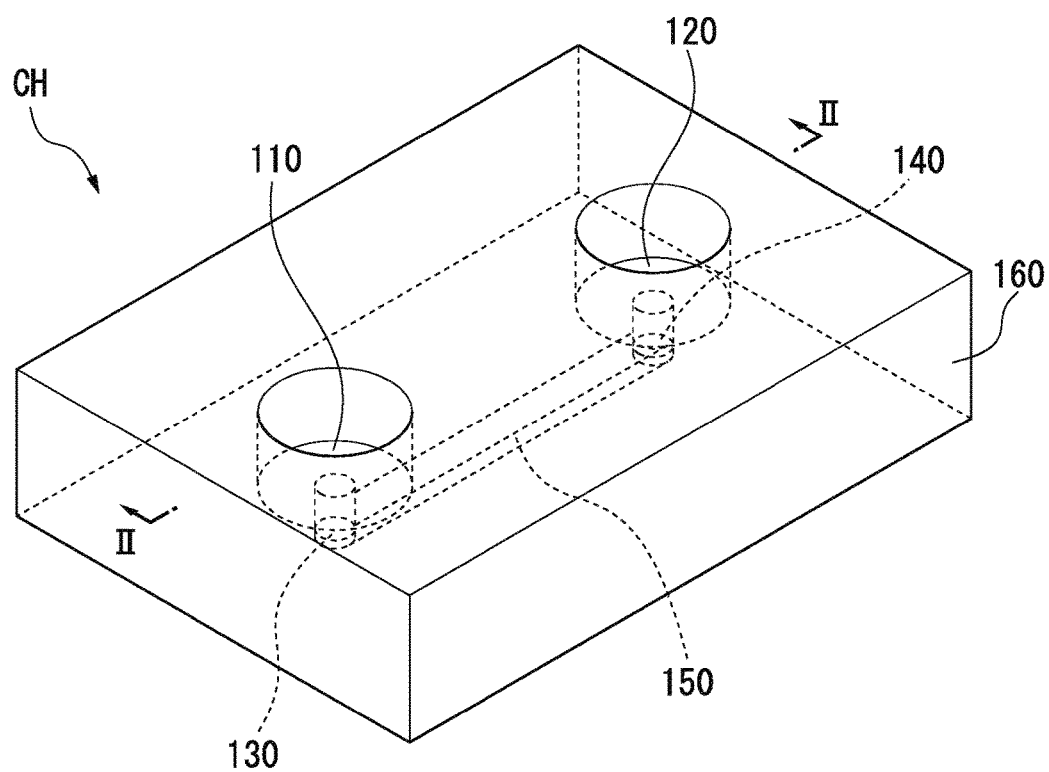
FIG. 3 is a perspective view of a basic structure of an extracellular endoplasmic reticulum analysis chip according to the present embodiment.
Figure 4:
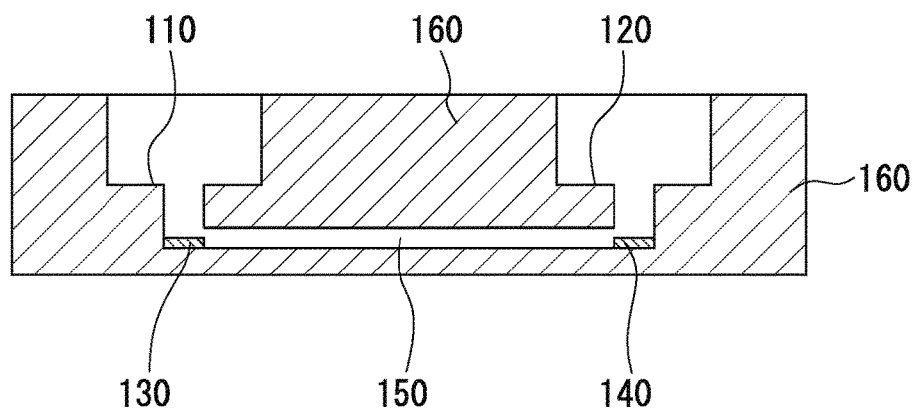
FIG. 4 is a cross-sectional view taken along the line II-II in FIG. 3.

FIG. 3 is a perspective view showing a basic structure of an extracellular endoplasmic reticulum analysis chip according to the embodiment. FIG. 4 is a cross-sectional view taken along the line II-II in FIG. 3. An extracellular endoplasmic reticulum analysis chip CH includes a first reservoir 110, a second reservoir 120, an electrophoresis flow path 150 connecting the first reservoir 110 to the second reservoir 120, and a base material 160. The electrophoresis flow path 150 is, for example, a milliflow path or a micro flow path. For example, the electrophoresis flow path 150 may have a size with a width of about 200 μm, a height of about 400 μm, and a length of about 10 mm. The cross section of the electrophoresis flow path 150 is not limited to a rectangular shape, and it may be, for example, a circular, elliptical, polygonal, or tunnel shaped. In the electrophoresis flow path 150, extracellular endoplasmic reticulum or a specific binding substance-extracellular endoplasmic reticulum complex (for example, an antibody-exosome complex) that is formed by interaction between a specific binding substance that specifically binds to a biological molecule present on the surface of the extracellular endoplasmic reticulum and the extracellular endoplasmic reticulum is electrophoresed. As an example of a specific binding substance, an antibody, an aptamer, or a combination thereof may be exemplified. Examples of an aptamer include a nucleic acid aptamer and a peptide aptamer. Examples of molecules recognized by a specific binding substance include antigens, membrane proteins, nucleic acids, sugar chains, and glycolipids.

The electrophoresis flow path 150 includes one end that is connected to the first reservoir 110 and the other end that is connected to the second reservoir 120. In addition, the first reservoir 110 and the second reservoir 120 are provided on the base material 160 and include an electrode 130 and an electrode 140, respectively. For example, the electrode 130 is provided on the bottom of the first reservoir 110 and the electrode 140 is provided on the bottom of the second reservoir 120. As shown in FIG. 4, the electrode 130 and the electrode 140 are provided in the vicinity of ends of the electrophoresis flow path 150. In addition, for example, a specimen (for example, analysis target exosome) is introduced into the first reservoir 110, and a buffer solution is introduced into the second reservoir 120. Here, the buffer solution may be introduced into the first reservoir 110.

The extracellular endoplasmic reticulum analysis chip CH is suitable for measuring a zeta potential of the extracellular endoplasmic reticulum. Hereinafter, a method of measuring a zeta potential of the exosome using an extracellular endoplasmic reticulum analysis chip will be described with an example in which an exosome as a specimen or the extracellular endoplasmic reticulum is analyzed.

First, a sample solution including an analysis target exosome is introduced into the first reservoir 110. The analysis target exosome may be an exosome having been reacted with a specific binding substance. The exosome may be, for example, an exosome extracted from a culture supernatant or a serum. The sample solution is, for example, an exosome suspension in which the exosome is suspended in a buffer solution such as phosphate buffered saline (PBS). Next, the sample solution including the exosome is introduced into the electrophoresis flow path 150. As an example, when a syringe is connected to the second reservoir 120 and the sample solution is sucked, it is possible to introduce the exosome into the electrophoresis flow path 150. Next, the buffer solution is put into the first reservoir 110 and the second reservoir 120. When liquid levels (liquid level heights) between the first reservoir 110 and the second reservoir 120 are adjusted and aligned according to a liquid level adjustment method to be described below, the generation of a hydrostatic pressure flow in the electrophoresis flow path 150 is prevented, and it is possible to improve an accuracy of zeta potential measurement. Next, a voltage is applied between the electrodes 130 and 140 by a control unit (for example, the control device 5 to be described below or a computer), and the exosomes are electrophoresed. As an example, the control unit applies a voltage with an electric field strength of about 50 V/cm for about 10 seconds.

During electrophoresis, a laser beam is emitted to the electrophoresis flow path 150, scattered light that is light emitted from the electrophoresis flow path 150 and has passed through the exosomes is condensed using an objective lens or the like, and the exosomes or the specific binding substance-exosome complex is imaged using a light receiving sensor (for example, a high sensitivity camera). The magnification of the objective lens is, for example, about 60. The wavelength and intensity of the laser are, for example, a wavelength of 405 nm and an intensity of 150 mW.

When the extracellular endoplasmic reticulum analysis chip in the present embodiment is used, not only an average value of zeta potential of a specific binding substance-exosome complex but also a zeta potential of a specific binding substance-exosome complex at a single particle level can be measured. Therefore, from the average value of the zeta potential, even in a case in which an exosome including a molecule (for example, an antigen) recognized by a specific binding substance is assumed not to be present in a sample, an exosome including an antigen as a minor population can be detected.

[Structure of Fluid Device C]

Figure 5:
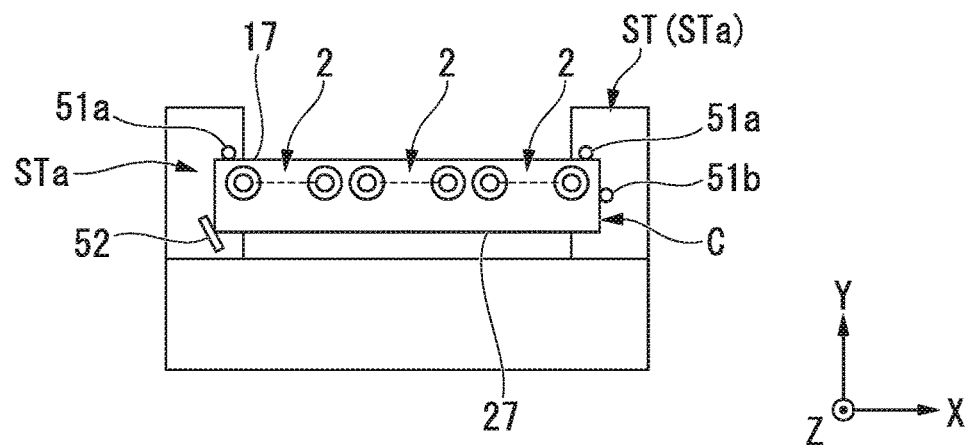
FIG. 5 is a plan view of a fluid device that is mounted on a mounting surface of a stage unit according to the present embodiment.
Figure 6:
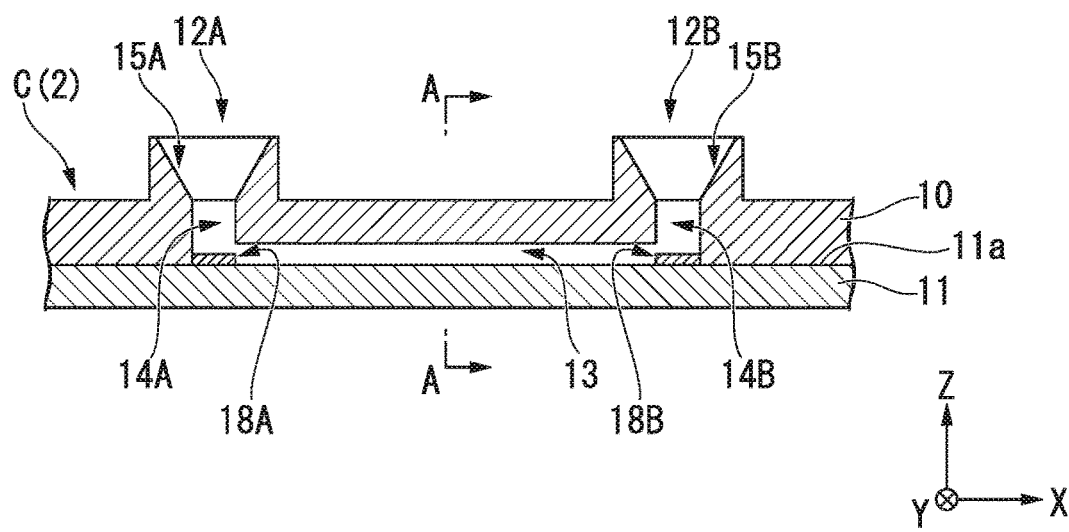
FIG. 6 is a partial cross-sectional view of the fluid device according to the present embodiment when partially sectioned on the yz plane.
Figure 7:
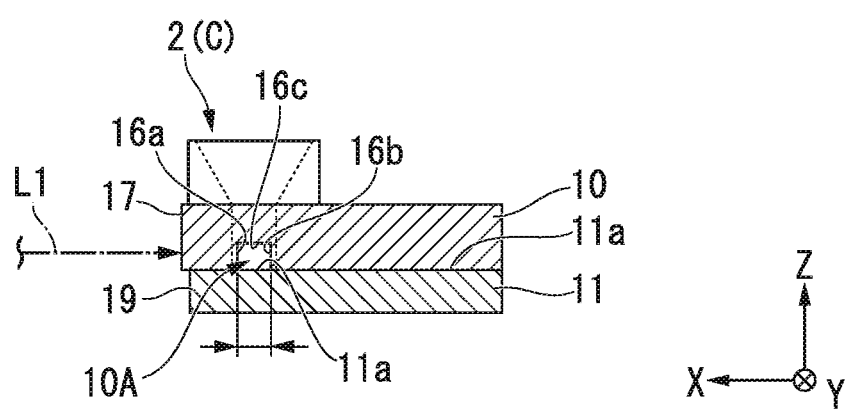
FIG. 7 is a cross-sectional view taken along the line A-A in FIG. 6.

FIG. 5 is a plan view of the fluid device C that is mounted on the mounting surface STa of the stage unit ST according to the embodiment. FIG. 6 is a partial cross-sectional view of the fluid device C according to the embodiment when partially sectioned on the xz plane. FIG. 7 is a cross-sectional view taken along the line A-A in FIG. 6.

As shown in FIG. 5, the fluid device C is formed in a rectangular shape in a plan view. As shown in FIG. 6, the fluid device C includes a reservoir member (first base material) 10 and a bottom plate (second base material) 11 which are sequentially stacked in the z direction. For example, the fluid device C in the present embodiment is a laminated structure (laminate) including at least the reservoir member 10 and the bottom plate 11.

In this case, the laminated structure of the fluid device C is a two-layer structure. In addition, for example, such a laminated structure of the fluid device C is formed by bonding the reservoir member 10 to the bottom plate 11.

The reservoir member 10 may be made of a material that is elastically deformable in at least one direction due to an external force or the like. The material of the reservoir member 10 is, for example, an elastomer, and silicone rubber, PDMS (polydimethylsiloxane), and the like may be exemplified. The bottom plate 11 may be made of a material through which the scattered light L2 generated according to emission of the illumination light L1 passes. The bottom plate 11 may be made of, for example, a glass material.

The fluid device C includes a plurality of lanes 2 (three lanes in FIG. 5) that are arranged in a length direction (x direction). The lanes 2 include a first reservoir 12A, a second reservoir 12B, a flow path 13, and electrodes 18A and 18B. The first reservoir 12A and the second reservoir 12B are disposed at intervals in the x direction. For example, the first reservoir 12A and the second reservoir 12B are disposed at intervals in the flow path direction of the flow path 13. In this manner, when the plurality of lanes are arranged in the flow path direction (in series), emission of light from the side becomes easier.

The plurality of lanes may be sequentially analyzed one lane at a time or may be simultaneously analyzed by a plurality of detection systems. Here, the plurality of lanes 2 may be arranged in the height direction (z direction).

In this case, a solution may be injected in the length direction (x direction) and may be injected in the y direction. For example, there are a plurality of emission light sources, and the light sources emit light to microparticles that flow in the lanes 2 with corresponding heights. In addition, a direction in which light is emitted from at least one emission light source is changed and thus light may be emitted to microparticles that flow in the lane 2.

Here, when there are a plurality of lanes 2, the shape of illumination light is adjusted by moving the objective lens, and thus illumination light emitted to the lanes 2 may be adjusted. In addition, when there are a plurality of lanes 2, the measurement target lane 2 may be selected from (switched) among the plurality of lanes 2 by movement of the stage on which the fluid device C is loaded.

The first reservoir 12A includes a retaining space 14A that has a circular cross section in a plane parallel to the xy plane and extends in the z direction and a funnel-shaped introduction unit 15A that gradually enlarges in diameter from the +z side end of the retaining space 14A toward the +z direction. The retaining space 14A has a −z side end that faces the bottom plate 11 and is open. The retaining space 14A is connected to the flow path 13.

The second reservoir 12B includes a retaining space 14B that has a circular cross section in a plane parallel to the xy plane and extends in the z direction and a funnel-shaped introduction unit 15B that gradually enlarges in diameter from the +z side end of the retaining space 14B toward the +z direction. The retaining space 14B has the −z side end that faces the bottom plate 11 and is open. The retaining space 14B is connected to the flow path 13.

The flow path 13 is an electrophoresis flow path (a flow path for electrophoresis). The flow path 13 extends in the y direction, which is the length direction of the fluid device C. The flow path 13 is provided to connect the retaining space 14A and the retaining space 14B to a surface side that faces the bottom plate 11. As shown in FIG. 7, the flow path 13 is formed in a rectangular cross section that is surrounded by a groove 10A formed in the reservoir member 10 and a surface (second surface) 11a of the bottom plate 11. The groove 10A is formed to be surrounded by side surfaces (first surfaces) 16a and 16b that face the x direction and a bottom surface (second surface) 16c that faces the surface 11a of the bottom plate 11 in the z direction. The side surfaces 16a and 16b, the bottom surface 16c and the surface 11a constituting the groove 10A are mirror-finished. The first surfaces include the side surface 16a, which is a first side surface, and the side surface 16b, which is a second side surface. The side surface 16a and the side surface 16b face each other and are separated from each other in the x direction, which is a first direction.

The lane 2 is disposed to deviate to the side close to an end surface 17 on the +x side relative to the center in an optical axis direction (incident direction) of the illumination light L1, which is the width direction of the fluid device C. The lane 2 is disposed to deviate to the side close to the end surface 17 on the incident side of the illumination light L1 relative to the center in the width direction (the x direction in FIG. 5) of the fluid device C, which is an optical axis direction of the incident illumination light L1. In the end surface 17, an area in which at least the lane 2 is provided in the y direction is mirror-finished. For example, the flow path 13 is formed to have a size with a width of about 200 μm, a height (the depth of the groove 10A) of about 400 μm, and a length of about 10 mm.

On the surface 11a of the bottom plate 11, the electrode 18A that faces the retaining space 14A is provided. On the surface 11a of the bottom plate 11, the electrode 18B that faces the retaining space 14B is provided. Materials of the electrode 18A and the electrode 18B may be gold, platinum, carbon, and the like. As shown in FIG. 7, an end surface (second end surface) 19 positioned on the incident side of the illumination light L1 on the bottom plate 11 is spaced to the −x side, which is the side opposite to the incident side of the illumination light L1 relative to a position on the end surface 17 of the reservoir member 10 in the x direction.

Returning to FIG. 1, as described above, the light source unit LS emits a laser beam with a wavelength that does not adversely influence particles, for example, a wavelength of 405 nm and an intensity of 150 mW, and a beam diameter (a diameter at which the intensity is 1/e2 with respect to the peak value) of 0.8 mm in the z direction as a deflection direction as the illumination light L1. Here, the illumination light L1 may be polarized light (for example, linearly polarized light) or non-polarized light. However, in the present embodiment, a configuration in which vertically polarized light is used, and there is no directivity of Rayleigh scattering is used.

The illumination light L1 is emitted to the fluid device C along the optical axis that extends in the direction intersecting the above-described orthogonal plane. In the present embodiment, the optical axis of the illumination light L1 is parallel to the x direction. The illumination light L1 of the present embodiment is emitted to the fluid device C along the optical axis that extends in the x direction.

Figure 8:
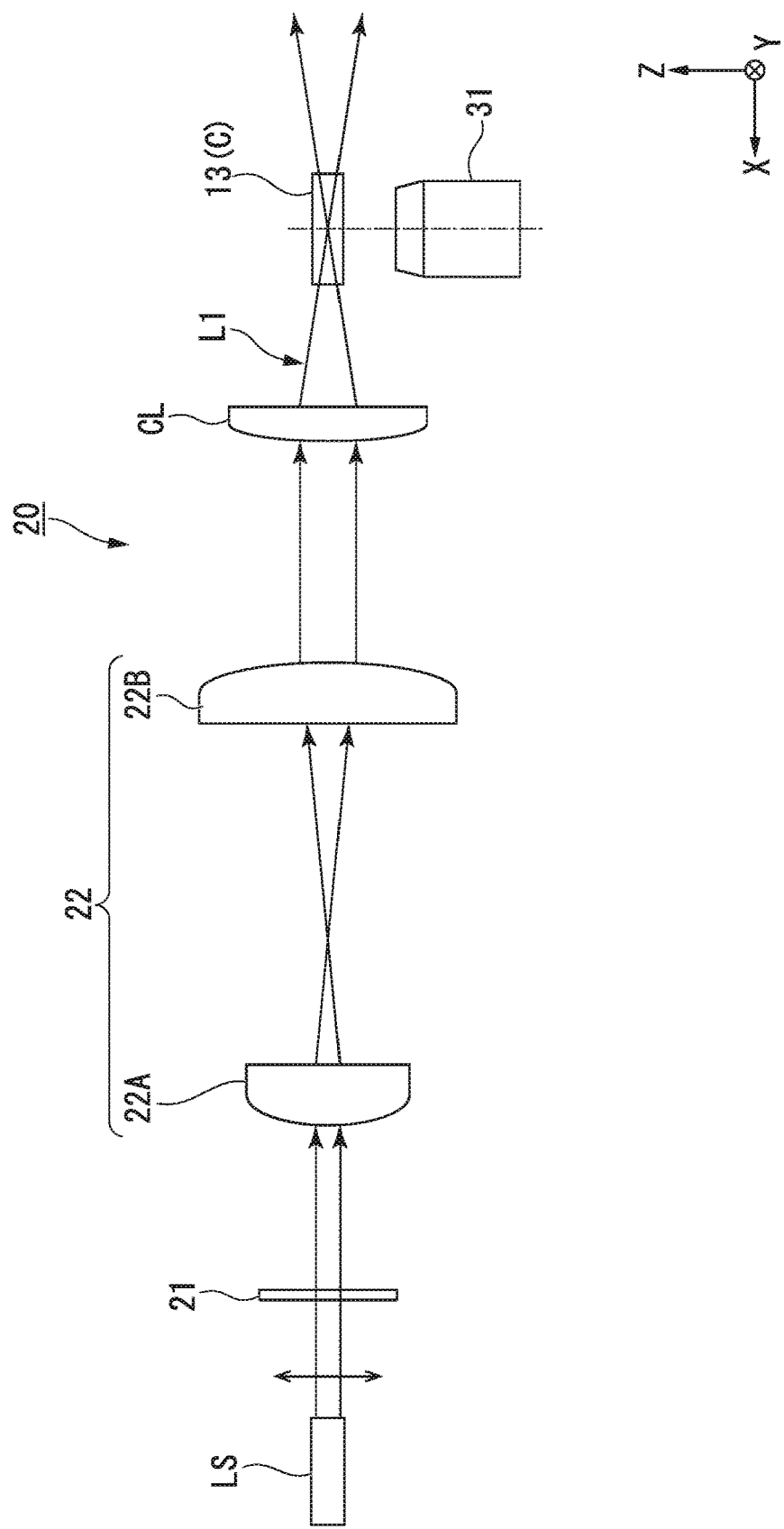
FIG. 8 is a diagram showing a schematic configuration of an emission unit and an adjustment unit according to the present embodiment.

FIG. 8 is a diagram showing a schematic configuration of the emission unit 20 and the adjustment unit CL according to the embodiment. The emission unit 20 includes a λ/2 plate 21 and an expander lens 22 that are sequentially disposed along the optical axis of the illumination light L1. Here, in the light source unit LS and the emission unit 20 shown in FIG. 1, the optical axis of the illumination light L1 extends in the y direction. However, since the illumination light L1 that is finally emitted to the fluid device C (the flow path 13) is on the optical axis in the x direction, the illumination light L1 whose optical axis is the x direction is shown in FIG. 8.

The illumination light L1 emitted from the light source unit LS passes through the λ/2 plate 21, and thus the polarization direction rotates in the y direction. Here, when the light source unit LS emits the illumination light L1 in the y direction as a deflection direction, the λ/2 plate 21 is unnecessary. The expander lens 22 includes cylindrical lenses 22A and 22B that are opposed to each other. Since the cylindrical lenses 22A and 22B have no power in the y direction, the width of the illumination light L1 in the y direction is constant. The width of the illumination light L1 in the z direction is enlarged or reduced according to the distance between the cylindrical lenses 22A and 22B in the optical axis direction. In the present embodiment, for example, the expander lens 22 enlarges the width of the illumination light L1 in the z direction by a factor of 2.

The adjustment unit CL adjusts the incident illumination light L1 with a width in the z direction enlarged by the expander lens 22. The adjustment unit CL is disposed on an optical path between the light source unit LS and an objective lens 31. In addition, the adjustment unit CL is disposed on an optical path between the λ/2 plate 21 or the expander lens 22 and the objective lens 31. The adjustment unit CL may include a drive mechanism and a light convergence point can be adjusted by movement of the adjustment unit CL. The adjustment unit CL can be driven, for example, in the x direction.

In this case, even if a chip on which the flow path 13 is in a different position is used, it is possible to perform adjustment so that the light convergence point is positioned within the flow path 13. In addition, adjustment may be performed so that the light convergence point is substantially coincident with the center of the flow path 13 or adjustment may be performed so that the center portion of the detection unit is substantially coincident with the light convergence point.

Figure 9:
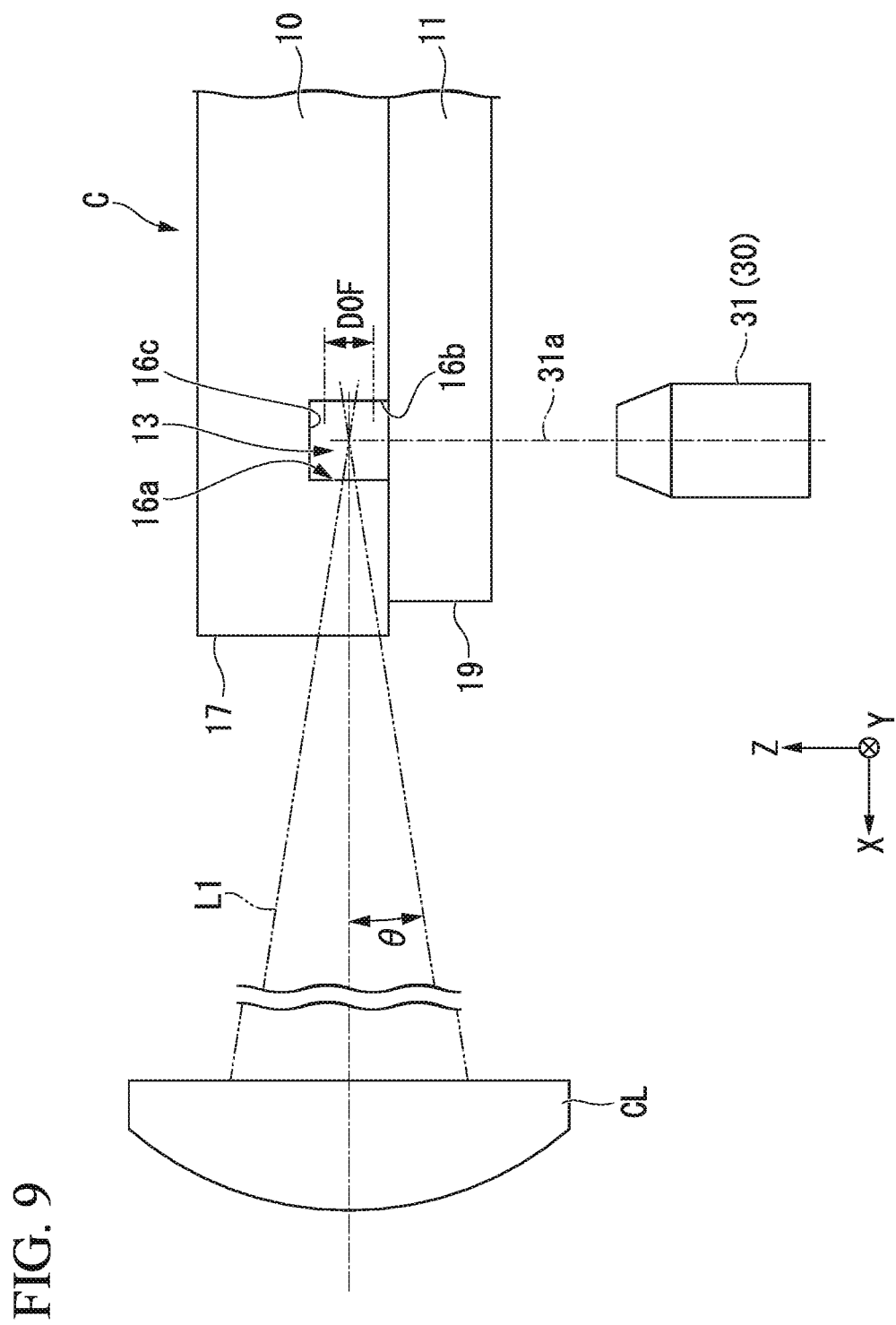
FIG. 9 is a partial detailed view of the adjustment unit and the fluid device according to the present embodiment.

FIG. 9 is a partial detailed view of the adjustment unit CL and the fluid device C according to the embodiment. The adjustment unit CL includes, for example, a cylindrical lens. The adjustment unit CL adjusts a convergence angle so that the width of the illumination light L1 in the z direction becomes a minimum inside the flow path 13 and a passage area of the illumination light L1 at a position on the side surface 16a on the emission light incident side of the flow path 13 converges to be confined within the side surface 16a. The adjustment unit CL performs adjustment so that the width of the illumination light L1 in the z direction becomes a minimum inside the flow path 13 and the illumination light L1 is adjusted to have a convergence angle at which an emission area of the illumination light L1 at a position on the side surface 16a on the emission light incident side of the flow path 13 converges on the side surface 16a. In addition, the adjustment unit CL adjusts a convergence angle so that a passage area of the illumination light L1 (emission light flux) at a position on the side surface 16b on the emission light exit side of the flow path 13 converges to be confined within the side surface 16b.

The adjustment unit CL adjusts the illumination light L1 to a convergence angle at which an emission area of the illumination light L1 (emission light flux) at a position on the side surface 16b on the emission light exit side of the flow path 13 converges on the side surface 16b.

In addition, the adjustment unit CL adjusts a convergence angle so that an emission area of the illumination light L1 at a position on the end surface 17 of the reservoir member 10 converges in the end surface 17. Further, the adjustment unit CL adjusts a convergence angle so that the illumination light L1 has a convergence point in a detection area in the flow path 13.

For example, an illumination light flux of the illumination light L1 outside the depth of focus of the detection unit 30 in the detection area of the flow path 13 has a smaller convergence angle than an illumination light flux within the depth of focus. Here for example, above-described orthogonal plane includes the end surface 17 of the reservoir member 10, the side surface 16a on the emission light incident side of the flow path 13, or the side surface 16b on the emission light exit side of the flow path 13.

Here, in the optical axis direction (x direction), when the width of the illumination light L1 in the z direction at the center (x=0) of the flow path 13 is the minimum width $\omega 0$, if the convergence angle of the illumination light L1 in the medium in the flow path 13 is $\theta$, the wavelength of the illumination light L1 is $\lambda$, the beam width in the z direction at the position x and the convergence angle $\theta$ is $\omega(x, \theta)$, the beam profile factor of the illumination light L1 is M2, and a distance from a position in the x direction at which the minimum width $\omega 0$ is reached to the side surface 16a is xL, it is necessary to satisfy the following Formula (3) and Formula (4), Formula (5).

[Math. 3]

$$\omega(x, \theta) = \omega_0 \cdot \sqrt{1 + \left(\frac{\lambda x M^2}{\pi \omega_0^2}\right)^2} \quad (3)$$

[Math. 4]

$$\omega_0 = \frac{\lambda M^2}{\pi \theta} \quad (4)$$

[Math. 5]

$$\frac{d\omega(x_L, \theta)}{d\theta} = 0 \quad (5)$$

Therefore, the adjustment unit CL that satisfies at least Formulae (3) to (5) and has optical properties in which the beam width $\omega(xL, \theta)$ at x=xL is smaller than the length of the side surface 16a in the z direction and the illumination light L1 is adjusted to converge at the convergence angle $\theta$ at which convergence occurs on the side surface 16a is mounted.

Here, when the illumination light L1 is Gaussian light, the beam width $\omega(x, \theta)$ included in the above Formulae (3) to (5) is defined as a width at which the intensity of the illumination light L1 is 1/e2 with respect to the peak value. Even if the convergence angle $\theta$ satisfies Formulae (1) to (3), since the illumination light L1 with an intensity that is 1/e2 or less with respect to the peak value enters a position on the side surface 16a outside the beam width $\omega(xL, \theta)$, the beam width of the illumination light L1 with an intensity that is 1/e2 or less with respect to the peak value is taken into consideration when the convergence angle $\theta$ is set.

Figure 10:
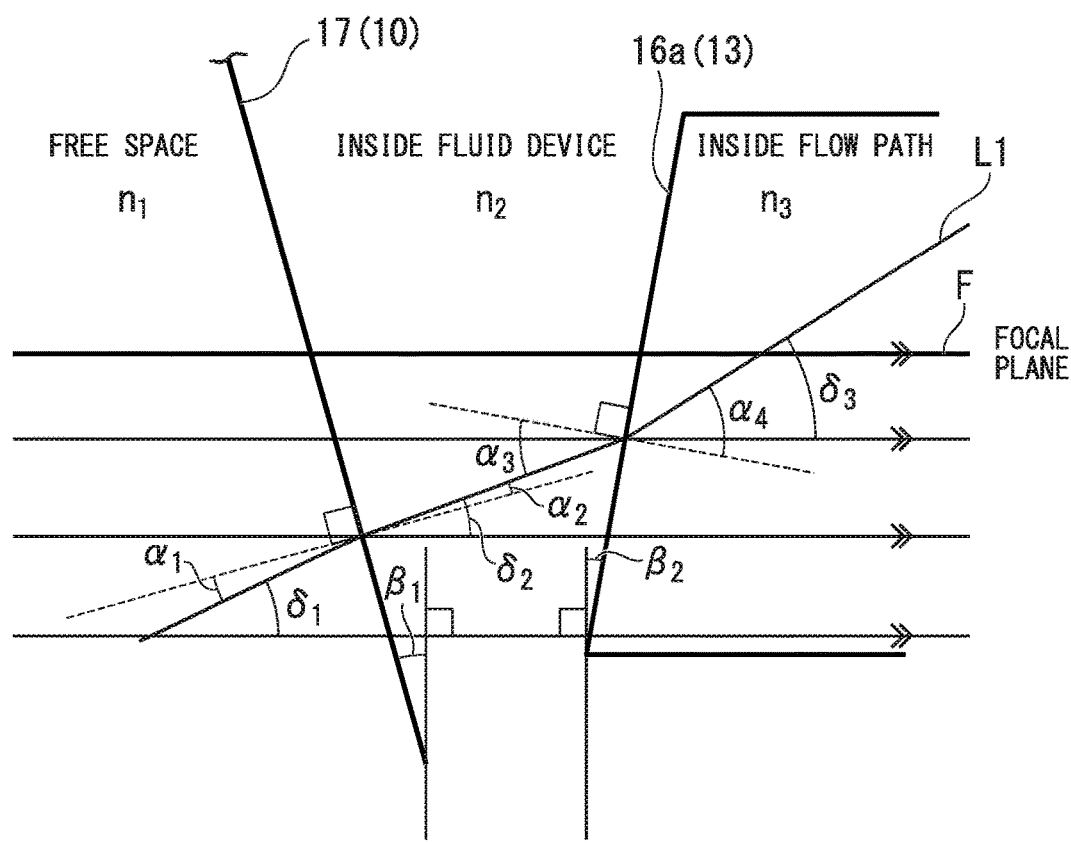
FIG. 10 is a diagram schematically showing an optical path through which illumination light according to the present embodiment passes through an end surface of a reservoir member and a side surface of a flow path.

In addition, in order for the detection unit 30 to set the entire area of the flow path 13 as a detection area in the optical axis direction (x direction) of the illumination light L1, it is necessary for the depth of focus DOF of the detection unit 30 to fall within the light flux of the illumination light L1 throughout the flow path 13. In order for the depth of focus DOF of the detection unit 30 to fall within the light flux of the illumination light L1 and for the depth of focus DOF of the detection unit 30 to fall within the light flux of the illumination light L1, it is necessary to also consider the inclination with respect to the optical axis of the end surface 17 of the reservoir member 10 and the side surface 16a of the flow path 13. FIG. 10 is a diagram schematically showing an optical path through which the illumination light L1 according to the embodiment passes through the end surface 17 of the reservoir member 10 and the side surface 16a of the flow path 13. In order for the depth of focus DOF (refer to FIG. 9) of the detection unit 30 to fall within the light flux of the illumination light L1 throughout the width of the flow path 13, it is necessary to satisfy the following Formula (6).

[Math. 6]

$$|\delta_3| \leq \left|\frac{\omega(x_L, \theta) - DOF/2}{x_L}\right| \quad (6)$$

Here, the angle $\delta 3$ is an elevation angle of the illumination optical axis seen from the focal plane F, and the counterclockwise direction from the focal plane F is defined as a positive direction. On the other hand, an incident angle and an exit angle at the interface, inclination angles of the end surface 17 of the reservoir member 10 and the side surface 16a of the flow path 13 with respect to the yz plane, elevation angles of illumination light flux in air, in the material of a flow path device C, and in the flow path with respect to the focal plane F, and refractive indexes of the medium outside the flow path device C, the material of the flow path device C, and the medium in the flow path 13 have the following relationships.

$n1 \sin \alpha1 = n2 \sin \alpha2$ $n2 \sin \alpha3 = n3 \sin \alpha4$ $\alpha1 + \beta1 = \delta1$ $\alpha2 + \beta1 = \delta2$ $$\alpha 3+\beta 2=\delta 2$$

$$\alpha 4+\beta 2=\delta 3$$

Here, α1: an incident angle of the illumination light L1 from a free space to the end surface 17 of the reservoir member 10

α2: an exit angle of the illumination light L1 from the end surface 17 into the reservoir member 10

α3: an incident angle of the illumination light L1 from the inside of the reservoir member 10 to the wall surface 16a of the flow path 13

α4: an exit angle of the illumination light L1 from the wall surface 16a into the flow path 13

β1: an inclination angle of the end surface 17

β2: an inclination angle of the wall surface 16a

δ1: an elevation angle of the illumination light L1 from the focal plane F in the free space δ2: an elevation angle of the illumination light L1 from the focal plane F in the reservoir member 10

δ3: an elevation angle of the illumination light L1 from the focal plane F in the flow path 13 n1: a refractive index in a free space medium n2: a refractive index of a material of the reservoir member 10 n3: a refractive index of a medium in the flow path 13, and incident angle and exit angle: an angle from the line perpendicular to the end surface 17 and the wall surface 16a inclination angle: an angle from the line perpendicular to the focal plane F elevation angle: an angle from the focal plane F.

In addition, all signs in the counterclockwise direction are positive.

From the above formulae, the elevation angle δ3 of the illumination light L1 in the flow path 13 is expressed by the following Formula (7).

[Math. 7]

$$\delta_3 = \sin^{-1}\left(\frac{n_2}{n_3}\sin\left(\left(\sin^{-1}\left(\frac{n_1}{n_2}\sin(\delta_1 - \beta_1)\right)\right) + \beta_1 - \beta_2\right)\right) + \beta_2 \quad (7)$$

Therefore, in order for the depth of focus DOF of the detection unit 30 to fall within the light flux of the illumination light L1 throughout the width of the flow path 13 in the x direction, it is necessary to satisfy the following Formula (8).

[Math. 8]

$$\left|\sin^{-1}\left(\frac{n_2}{n_3}\sin\left(\left(\sin^{-1}\left(\frac{n_1}{n_2}\sin(\delta_1 - \beta_1)\right)\right) + \beta_1 - \beta_2\right)\right) + \beta_2\right| \leq \quad (8)$$

$$\left|\frac{\omega(x_L, \theta) - DOF/2}{x_L}\right|$$

Therefore, it is necessary to perform selection, manufacturing, and adjustment so that inclination angles of the end surface 17 of the reservoir member 10 and the wall surface 16a of the flow path 13, and the elevation angle δ3 of the illumination light L1 satisfy Formula (8) according to the refractive index n1 of the free space medium, the refractive index n2 of the material of the reservoir member 10, and the refractive index n3 of the medium in the flow path 13.

The stage unit ST moves in the x direction, the y direction, and the z direction according to driving of a stage drive unit 60 shown in FIG. 2. Driving of the stage drive unit 60 is controlled by the control device 5.

As shown in FIG. 5, the stage unit ST includes the mounting surface STa on which the fluid device C is mounted. The mounting surface STa is a surface parallel to the xy plane. The mounting surface STa may be disposed at intervals in the y direction. The mounting surface STa supports both ends in the y direction in which the lane 2 of the flow path device C is not provided from the −Z side. In the fluid device C, an area in which the lane 2 is disposed is supported on the mounting surface STa without hindering observation by the detection unit 30 from the −Z side. In addition, since there is no stage unit ST on the optical path of the illumination light L1 until light is emitted to the lane 2 in the fluid device C, it is possible to prevent some of the illumination light L1 incident on the fluid device C from entering the stage unit ST and adversely influencing particle detection to be described below.

Fixed pins 51 are provided to protrude from the mounting surface STa. The fixed pins 51 include two fixed pins 51a in contact with the long side of the fluid device C and one fixed pin 5b in contact with the short side of the fluid device C. The fixed pins 51a are disposed in the vicinity of both sides of the fluid device C in the y direction. The fixed pin 51b comes in contact with the short side positioned on the +y side. The pressing piece 52 is provided at a corner positioned diagonally with respect to a corner at which the fixed pins 51a and the fixed pin 51b positioned on the +y side are disposed. The pressing piece 52 presses the fluid device C in the diagonal direction with respect to the stage unit ST. The pressed fluid device C is positioned on the stage unit ST in the xy direction so that the flow path 13 (the lane 2) is parallel to the y direction when in contact with the fixed pins 51a and 51b and fixed.

The detection unit 30 includes the objective lens 31 and an imaging unit 32. The objective lens 31 is disposed on the −Z side of the stage unit ST and the fluid device C. As shown in FIG. 9, the objective lens 31 is disposed at a position at which a detection axis 31a passes through the center of the flow path 13 in the x direction. The detection axis 31a is orthogonal to the optical axis of the illumination light L1. The imaging unit 32 includes, for example, an electron multiplying charge coupled device (EMCCD) camera, and captures an image of incident light. The imaging unit 32 acquires image information of side-scattered light incident through the objective lens 31.

The transmission unit 40 transmits information about the image captured by the imaging unit 32 to the control device 5.

[Operation of Particle Detection Device]

The operation of the particle detection device 100 includes a mounting process, an introducing process, an emitting process, and a detecting process.

The mounting process is a process in which the fluid device C is mounted on the mounting surface STa of the stage unit ST.

Specifically, as shown in FIG. 5, when the fluid device C is pressed in the diagonal direction by the pressing piece 52, the fluid device C is pressed against the fixed pins 51a and 51b and is mounted on the mounting surface STa while it is positioned on the stage unit ST so that the flow path 13 (the lane 2) is parallel to the y direction.

The introducing process is a process in which a sample containing particles is introduced into the retaining spaces 14A and 14B, and the flow path 13 of the fluid device C. As a sample, for example, an exosome suspension in which an exosome is suspended in a buffer solution (medium) such as a phosphate buffer solution can be used.

When the sample is introduced into the flow path 13, the control device 5 drives the stage drive unit 60, and the detection target lane 2 is positioned on the optical path of the illumination light L1 and the detection axis 31a of the detection unit 30.

When the detection target lane 2 moves to a detection position, the control device 5 controls a power supply unit BT, applies an electric field to the electrode 18A and the electrode 18B, and imparts a force with which the exosomes are electrophoresed along the flow path 13. For example, the control device 5 applies a voltage with an electric field strength of about 50 V/cm for about 10 seconds. A movement direction of the exosomes is parallel to the y direction.

The emitting process is a process in which the illumination light L1 is emitted to the flow path 13 of the flow path device C parallel to the x direction.

The emission unit 20 and the adjustment unit CL that emit the illumination light L1 emit the illumination light L1 in the form of a sheet beam that has a constant width in the y direction and converges in the z direction at a convergence angle θ that satisfies the above-described Formula (3) to Formula (8). The minimum beam thickness (beam width in the z direction) of the illumination light L1 is, for example, 10 μm. The direction of the minimum beam thickness (beam width in the z direction) of the illumination light L1 is a direction parallel to the z direction or the z direction in FIG. 7 and FIG. 9. The direction of the minimum beam thickness (beam width in the z direction) of the illumination light L1 is a direction different from the optical axis direction and the flow path direction of the illumination light L1 on the incident surface (the end surface 17 and the side surface 16a), and is a direction orthogonal to the optical axis direction and the flow path direction. The flow path direction is a direction in which the flow path 13 extends. The flow path direction is a direction in which a fluid flows through the flow path 13.

The emitted illumination light L1 sequentially passes through one end surface (an end surface on the illumination light incident side) 17 of the fluid device C, the side surface (a side surface on the illumination light incident side) 16a of the flow path 13, the inside of the flow path 13, the side surface (a side surface on the illumination light exit side) 16b of the flow path 13, and the other end surface (an end surface on the illumination light exit side) 27 (refer to FIG. 5) of the fluid device C. The illumination light L1 is emitted in a direction orthogonal to the movement direction of the exosomes.

As shown in FIG. 9, the emitted illumination light L1 converges so that the width in the z direction becomes a minimum inside the flow path 13 and a passage area of the emission light flux at a position on the side surface 16a of the flow path 13 converges to be confined within the side surface 16a. Further, the emitted illumination light L1 converges so that a passage area of the emission light flux at a position on the side surface 16b on the illumination light exit side of the flow path 13 is confined to be within the side surface 16a. The illumination light L1 is adjusted to have a convergence angle at which an emission area at a position on the side surface 16a converges on the side surface 16a and an emission area at a position on the side surface 16b converges on the side surface 16b. In addition, the emitted illumination light L1 has a convergence point in a detection area of the detection unit 30 in the flow path 13.

In the detecting process, scattered light generated from particles inside the flow path 13 when the illumination light L1 is emitted parallel to the x direction is observed (imaged) and detected by the detection unit 30. Since the detection axis 31a of the objective lens 31 in the detection unit 30 is orthogonal to the optical axis of the illumination light L1, the detection unit 30 detects side-scattered light generated from the particles. According to emission of the illumination light L1 that is emitted parallel to the x direction, the detection unit 30 detects light scattered in the z direction perpendicular to the x direction. An image of particles in which scattered light is observed is captured by the imaging unit 32. The transmission unit 40 transmits information about the image captured by the imaging unit 32 to the control device 5.

[Configuration of Control Device]

The control device 5 collectively controls the particle detection system 1. The control device 5 controls movement of the stage unit ST and the fluid device C through the stage drive unit 60. The control device 5 controls a power supply unit (application unit) BT, and applies an electric field to the electrodes 18A and 18B in the direction along the flow path 13. In addition, the control device 5 processes an image captured by the particle detection device 100 and performs various types of determination. A configuration of the control device 5 will be described in detail with reference to FIG. 11 to FIG. 16.

Figure 11:
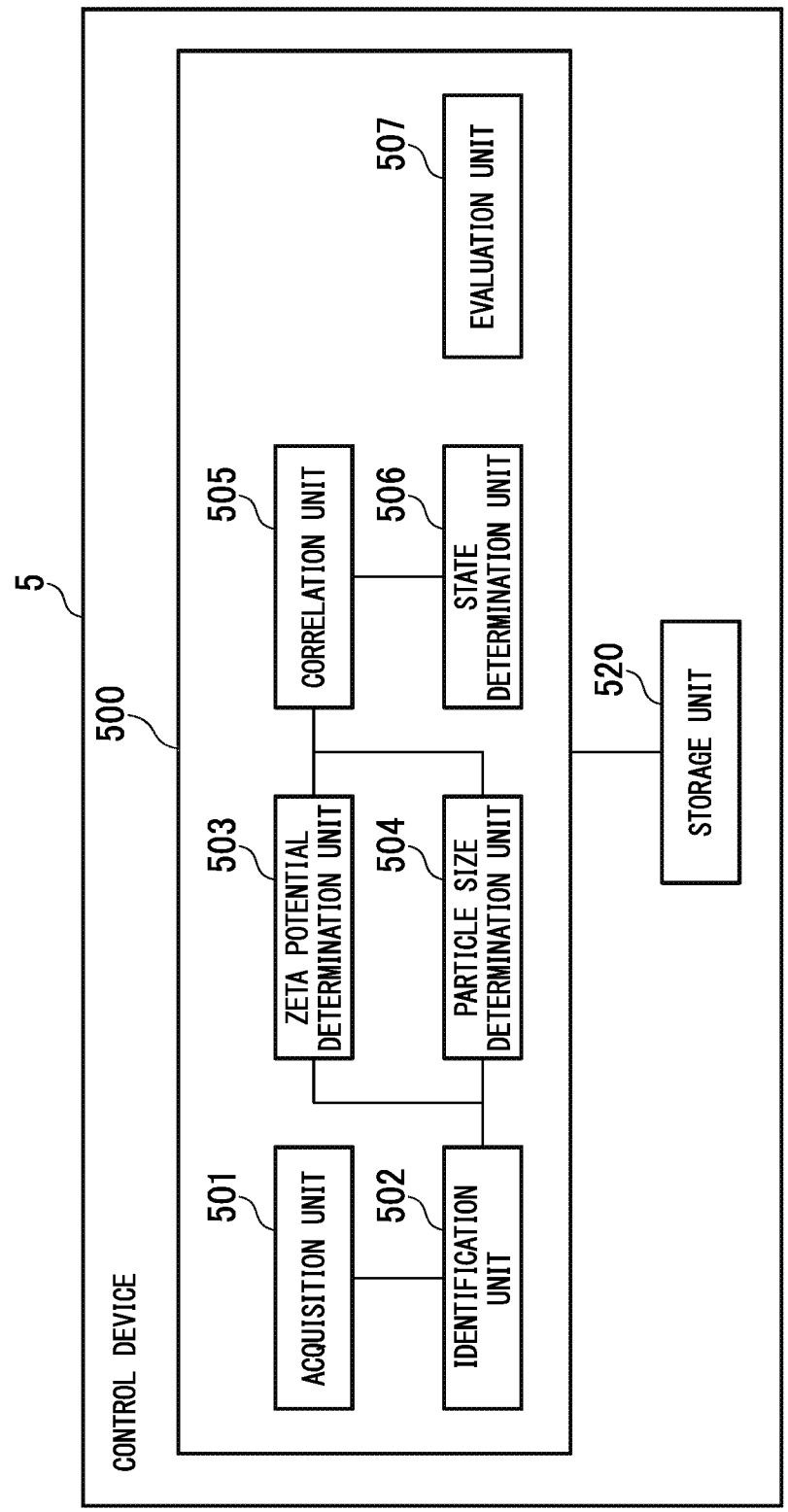
FIG. 11 is a diagram showing a schematic configuration of a control device according to the present embodiment.

FIG. 11 is a diagram showing a schematic configuration of the control device 5 of the present embodiment. The control device 5 includes an operation unit 500 and a storage unit 520. The storage unit 520 includes a storage device such as a flash memory, a hard disk drive (HDD), a random access memory (RAM), a read only memory (ROM), and a register. A program (firmware) that the operation unit 500 executes is stored in advance in the storage unit 520. In addition, operation results obtained by operation processing of the operation unit 500 are stored in the storage unit 520.

The operation unit 500 includes a central processing unit (CPU), and performs various operations. The operation unit 500 includes an acquisition unit 501, an identification unit 502, a zeta potential determination unit 503, a particle size determination unit 504, a correlation unit 505, a state determination unit 506, and an evaluation unit 507 as functional units.

The acquisition unit 501 acquires an image captured by the particle detection device 100. Specifically, as described above, the imaging unit 32 of the particle detection device 100 captures an image of incident side-scattered light through the objective lens 31 and outputs image information about the captured image to the transmission unit 40. The acquisition unit 501 acquires image information about the image of side-scattered light captured by the imaging unit 32 through the transmission unit 40. The acquisition unit 501 outputs the acquired image to the identification unit 502.

The identification unit 502 extracts an image of microparticles from images captured by the particle detection device 100. For example, the identification unit 502 performs known filtering processing and a pattern matching processing on the image supplied from the acquisition unit 501 and thus extracts the image of microparticles. In this case, the identification unit 502 may assign a particle number for each microparticle for the extracted microparticle image. Here, when an identification target microparticle is extracellular endoplasmic reticulum, the particle number may be an identifier of the extracellular endoplasmic reticulum. That is, the identification unit 502 may perform labeling on particles of microparticles. Therefore, in the correlation unit to be described below, association between the zeta potential ζ of the microparticle and the particle size d of the microparticle becomes easier. During this labeling, it may be determined whether an image of a first microparticle included in an image captured at a first time and an image of a second microparticle included in an image captured at a second time that is different from the first time among a plurality of images acquired by the acquisition unit are images showing the same microparticle on the basis of the movement amount of the microparticle due to Brownian motion in the medium. In addition, the identification unit 502 performs tracking of the labeled particles of microparticles on the basis of differences between frames of the image captured by the particle detection device 100. Here, tracking refers to tracking of a change in coordinates of particles in the image over time. An example of results obtained by the identification unit 502 tracking microparticles is shown in FIG. 12.

FIG. 12 is a diagram showing an example of a particle list LS1 stored in the storage unit 520 of the present embodiment. In the particle list LS1, coordinates (X, Y) of microparticle images at each time are stored with a labeled particle number in the row direction and an imaging time in the column direction. In this example, coordinates of microparticles including a microparticle P1 to a microparticle Pn at times from a time t0 to a time t50 are stored in the particle list LS1.

Returning to FIG. 11, the zeta potential determination unit 503 determines the zeta potential $\zeta$ for each microparticle on the basis of the tracking results obtained by the identification unit 502. For example, the zeta potential determination unit 503 determines a zeta potential $\zeta 1$ of the microparticle P1 on the basis of a movement speed v1 of the microparticle P1 from the time t0 to the time t1 among results obtained by tracking the microparticle P1 by the identification unit 502.

The zeta potential determination unit 503 determines the zeta potential on the basis of the above-described Formula (1). Here, in this example, a dielectric constant c of the sample solution and a viscosity coefficient $\eta$ of the sample solution are stored in the storage unit 520 in advance. The zeta potential determination unit 503 determines the zeta potential $\zeta$ of the microparticle on the basis of the dielectric constant c of the sample solution and the viscosity coefficient $\eta$ of the sample solution stored in the storage unit 520 and the movement speed of the microparticle obtained from the tracking results obtained by the identification unit 502.

The particle size determination unit 504 determines the diameter of the microparticle on the basis of the movement amount of the microparticle due to Brownian motion in the sample solution and the above-described Formula (2). Here, a specific example in which the particle size determination unit 504 determines the particle size of the microparticle P1 will be described. Here, in this example, the Boltzmann constant k and an absolute temperature T of the sample solution are stored in the storage unit 520 in advance. The particle size determination unit 504 calculates the movement amount of the microparticle P1 on the basis of the tracking results obtained by the identification unit 502. In addition, the particle size determination unit 504 determines a particle size d1 of the microparticle P1 on the basis of the calculated movement amount of microparticle P1 and the Boltzmann constant k and the absolute temperature T stored in the storage unit 520 and the above-described Formula (2).

The correlation unit 505 associates the zeta potential $\zeta$ of the microparticle determined by the zeta potential determination unit 503 with the particle size d of the microparticle determined by the particle size determination unit 504. Specifically, the first zeta potential $\zeta 1$ determined for the first microparticle in the zeta potential determination unit 503 and the first particle size d1 determined for the first microparticle in the particle size determination unit 504 are associated with each other as data regarding the first microparticle in the correlation unit 505. FIG. 13 shows an example of a particle correlation list LS2 which shows association results obtained by the correlation unit 505.

FIG. 13 is a diagram showing an example of a particle correlation list LS2 stored in the storage unit 520 of the present embodiment. In the particle correlation list LS2, the particle size d and zeta potential $\zeta$ are associated with each other for each particle number assigned by the identification unit 502. Regarding the microparticle P1, the correlation unit 505 associates the particle size d1 of the microparticle P1 with the zeta potential $\zeta 1$ of the microparticle P1 and stores it as particle correlation information PC1 (d1, $\zeta 1$) in the particle correlation list LS2. In addition, regarding the microparticle P2, the correlation unit 505 associates a particle size d2 of the microparticle P2 with a zeta potential $\zeta 2$ of the microparticle P2, and stores it as particle correlation information PC2 (d2, $\zeta 2$) in the particle correlation list LS2.

In this manner, according to the present embodiment, it is possible to determine the correlation of states of microparticles present in the medium.

The state determination unit 506 determines a state of a microparticle on the basis of the particle correlation list LS2 generated by the correlation unit 505. In the storage unit 520, reference range information indicating a reference range of the particle size d and a reference range of the zeta potential $\zeta$ are stored. Here, as an example of determining a state by the state determination unit 506, a case in which, in a sample containing particles other than an exosome, it is determined whether a microparticle identified by the identification unit 502 is an exosome will be described.

Features of an exosome include that it is a microparticle with a particle size of about 30 to 200 nm in diameter and chaperone molecules Hsc70 and Hsc90, and tetraspanin (CD9, CD63, and CD81) are specifically present as constituent factors.

In this case, in the storage unit 520, a threshold value Thd of the particle size is stored as reference range information. In addition, in the storage unit 520, a threshold value Th$\zeta$ of the zeta potential is stored as reference range information. In such cases, the storage unit 520 may be referred to as a reference storage unit. Examples of the threshold value Thd and the threshold value Th$\zeta$ are shown in FIG. 14.

Figure 14:
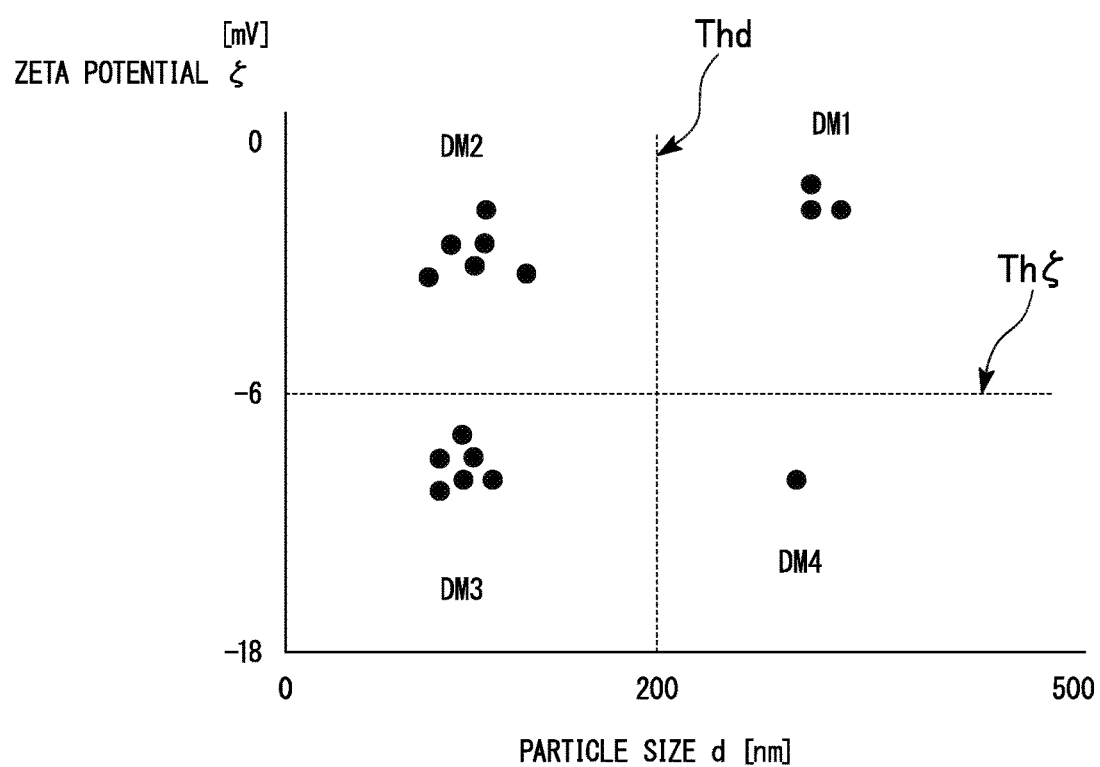
FIG. 14 is a diagram showing an example of threshold values stored in the storage unit of the present embodiment.

FIG. 14 is a diagram showing an example of threshold values stored in the storage unit 520 of the present embodiment. Here, as an example, a case in which an exosome has a particle size of about 30 to 100 nm in diameter and among determination target microparticles, microparticles other than an exosome have a particle size that exceeds 100 nm in diameter will be described. In addition, here, as an example, a case in which the zeta potential $\zeta$ of the exosome is equal to or less than the threshold value Th$\zeta$ and the zeta potential $\zeta$ of microparticles other than the exosome exceeds the threshold value Th$\zeta$ will be described. In this example, the state determination unit 506 can determine a microparticle on the basis of the particle size of the microparticle and the zeta potential $\zeta$ of the microparticle. Here, the determination of the microparticle performed by the state determination unit 506 may be referred to as identification of a microparticle.

Specifically, in this example, in the storage unit 520, 100 nm is stored as the threshold value Thd of the particle size. In addition, in the storage unit 520, −6 mV is stored as the threshold value Th$\zeta$ of the zeta potential. The state determination unit 506 determines that a microparticle whose particle size d is equal to or less than threshold value Thd and that a microparticle whose zeta potential ζ is equal to or less than the threshold value Thζ within the particle correlation information PC stored in the particle correlation list LS2 is an exosome. On the other hand, the state determination unit 506 determines that a microparticle whose particle size d exceeds the threshold value Thd or a microparticle whose zeta potential ζ exceeds the threshold value Thζ within the particle correlation information PC stored in the particle correlation list LS2 is not an exosome.

In addition, as an example, a case in which the particle size of an exosome is about 30 to 100 nm in diameter, and among determination target microparticles, the particle size of microparticles other than an exosome exceeds 200 nm in diameter will be described. In this case, as an example, when the threshold value Thd of the particle size d is set to 150 nm, the state determination unit 506 can determine a state of the microparticle on the basis of only the particle size.

In addition, microparticles other than the exosome may be included in a range of 100 to 200 nm in diameter. In this case, the threshold value Thd (200 nm) of the particle size can be used as a factor for determining whether a microparticle is an exosome.

In addition, in a range in which the diameter is larger than 200 nm, a single exosome may not be included. In this case, the threshold value Thd (200 nm) of the particle size can be used as a factor for determining whether a microparticle is a single exosome.

In addition, in a range in which the diameter is larger than 200 nm, a microparticle in which a plurality of single exosomes are aggregated may be included. In this case, the threshold value Thd (200 nm) of the particle size can be used as a factor for determining whether a microparticle is a single exosome or an aggregated exosome.

In this manner, the threshold value serving as a reference value stored in the reference storage unit can be used as a factor for determining a state of a microparticle.

In addition, when the microparticle identified by the identification unit 502 is an exosome, the state determination unit 506 determines whether the exosome reacts with an antibody. In this example, in the storage unit 520, the threshold value Thζ of the zeta potential is stored as reference range information. As described above, the zeta potential of the antibody-exosome complex is shifted positively compared to the zeta potential of the exosomes alone. In this case, in the storage unit 520, a zeta potential (for example, −6 my) between the zeta potential of the exosome alone and the zeta potential of the antibody-exosome complex is stored as the threshold value Thζ of the zeta potential. The state determination unit 506 determines that a microparticle whose zeta potential is less than the threshold value Thζ within the particle correlation information PC stored in the particle correlation list LS2 is a single exosome that does not react with an antibody. On the other hand, the state determination unit 506 determines that a microparticle whose zeta potential is equal to or greater than the threshold value Thζ within the particle correlation information PC stored in the particle correlation list LS2 is an antibody-exosome complex.

In addition, microparticles other than a single exosome and an antibody-exosome complex may be present in the vicinity of the threshold value Thζ (for example, −6 mV) of the zeta potential. In this case, the threshold value Thζ (−6 mV) of the zeta potential can be used as a factor for determining whether a microparticle is a single exosome.

In addition, the state determination unit 506 can determine a state of a microparticle from a combination of the threshold value of the particle size d and the threshold value of the zeta potential ζ. Specifically, an antibody-exosome complex has a lower zeta potential than a single exosome. Therefore, an antibody-exosome complex has a weaker Coulomb force acting between microparticles than a single exosome. The Coulomb force acting between microparticles acts as a repulsive force maintaining an interval between microparticles. That is, an antibody-exosome complex has a weaker repulsive force acting between microparticles than a single exosome. Therefore, an antibody-exosome complex is more likely to aggregate than a single exosome. Here, when microparticles aggregate, since a plurality of aggregated microparticles act as one microparticle, a change occurs in the momentum of Brownian motion. Thus, the particle size determination unit 504 determines a plurality of aggregated microparticles as one microparticle, and thus performs shifting in a direction in which the particle size d increases compared to when microparticles are not aggregated.

Here, a case in which a microparticle with a particle size d of 200 nm or less is determined as an exosome will be described as an example. The particle size determination unit 504 may determine that an antibody-exosome complex is a microparticle with a diameter that exceeds 200 nm. Therefore, when the state determination unit 506 performs determination using only the particle size d, since the particle size d of the antibody-exosome complex exceeds the threshold value Thd of the particle size d for determination whether it is an exosome, it may be determined that the antibody-exosome complex is not an exosome. Therefore, even if it is determined that a microparticle with a particle size d of 200 nm or less is an exosome and a microparticle has a particle size d that exceeds 200 nm, when the zeta potential ζ is equal to less than the threshold value Thζ, the state determination unit 506 determines that the microparticle is an exosome. That is, the state determination unit 506 determines whether a microparticle is an exosome from a combination of the threshold value Thd of the particle size d and the threshold value Thζ of the zeta potential ζ.

In addition, for determination of whether a microparticle is an exosome, an antibody that specifically binds to an exosome such as tetraspanin (such as CD9 and CD81) can be used.

That is, it is possible to determine whether a microparticle is an exosome on the basis of changes in the zeta potential ζ and the particle size d occurring when the antibody acts with the exosome.

The particle detection system 1 of the present embodiment has an advantage in that it is possible to evaluate a microparticle in various combinations of the above-described evaluation conditions based on the zeta potential ζ and the particle size d.

In addition, the state determination unit 506 combines the threshold value Thd of the particle size d and the threshold value Thζ of the zeta potential ζ and then can determine a state of a microparticle on the basis of tracking results obtained by the identification unit 502. Specifically, the state determination unit 506 tracks progress in which an single exosome reacts with an antibody and further antibody-exosome complexes aggregate on the basis of tracking results obtained by the identification unit 502. Specifically, the state determination unit 506 determines a state of a microparticle according to movement from an area to an area of the particle size d and the zeta potential ζ of the microparticles among an area DM1 to an area DM4 shown in FIG. 14 with the passage of time. As an example, when a microparticle (for example, single exosome) present in the area DM3 moves to the area DM2, the state determination unit 506 determines that the exosome has reacted with an antibody and has changed to an antibody-exosome complex. In addition, when the exosome moves from the area DM2 to the area DM1, the state determination unit 506 determines that antibody-exosome complexes have aggregated.

The evaluation unit 507 evaluates the quality of the state of the microparticle. As an example, the evaluation unit 507 ranks the state of the microparticle as a rank A, a rank B, or a rank C on the basis of the state of the microparticle determined by the state determination unit 506. Here, the rank A corresponds to a case in which both the particle size d and the zeta potential $\zeta$ of the microparticle are included in the reference range. In addition, the rank B corresponds to a case in which either of the particle size d and the zeta potential $\zeta$ of the microparticle is not included in the reference range. In addition, the rank C corresponds to a case in which neither the particle size d nor the zeta potential $\zeta$ of the microparticle is included in the reference range.

As an example, a case in which the evaluation unit 507 evaluates whether a microparticle is a single exosome will be described. In this case, when a microparticle is present in the area DM3, the evaluation unit 507 determines that the rank of the microparticle is the rank A. In addition, when a microparticle is present in the area DM2 or the area DM4, the evaluation unit 507 determines that the rank of the microparticle is the rank B. In addition, when a microparticle is present in the area DM1, the evaluation unit 507 determines that the rank of the microparticle is the rank C.

[Operation of Control Device]

Next, an operation of the control device 5 will be described with reference to FIG. 15.

Figure 15:
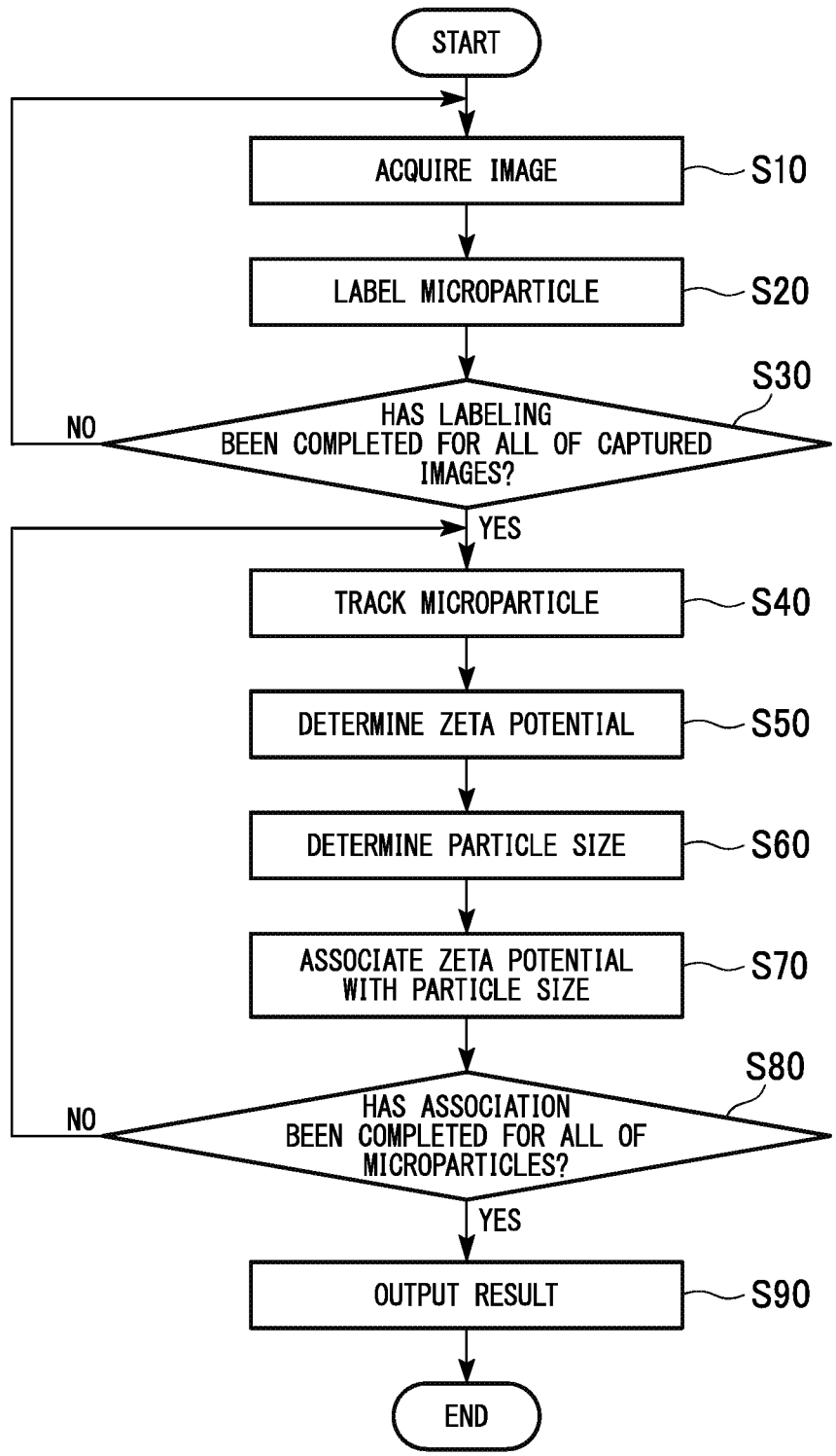
FIG. 15 is a diagram showing an example of operations of a control device of the present embodiment.

FIG. 15 is a diagram showing an example of an operation of the control device 5 of the present embodiment. Here, a case in which the particle detection device 100 captures an image of side-scattered light at predetermined time intervals will be described.

The acquisition unit 501 acquires the images captured by the imaging unit 32 of the particle detection device 100 from the particle detection device 100 one by one (Step S10). In the images, an image of a microparticle that electrophoreses along the electrophoresis flow path 150 is included. In addition, in the image of a microparticle, an image of an exosome is included.

Next, the identification unit 502 extracts the image of a microparticle from the image acquired in Step S10 and assigns a unique particle number for each microparticle. That is, the identification unit 502 labels the microparticle (Step S20). The identification unit 502 determines whether labeling has been completed for all of the captured images (Step S30). When it is determined that labeling has not been completed for all of the captured images (Step S30; NO), the process returns to Step S10, and the identification unit 502 performs labeling on the next image. When it is determined that labeling has been completed for all of the captured images (Step S30; YES), the process advances to Step S40, and the identification unit 502 performs tracking on the identified microparticle.

Next, the zeta potential determination unit 503 determines the zeta potential $\zeta$ for each microparticle on the basis of the tracking results obtained by the identification unit 502 (Step S50). In addition, the particle size determination unit 504 determines a particle size for each microparticle on the basis of the tracking results obtained by the identification unit 502 (Step S60). Here, Step S50 and Step S60 may be reversed in order or may be performed in parallel.

Next, the correlation unit 505 associates the zeta potential of the microparticle determined by the zeta potential determination unit 503 with the particle size d of the microparticle determined by the particle size determination unit 504 (Step SS70).

The correlation unit 505 generates the particle correlation list LS2 indicating association results and stores the generated particle correlation list LS2 in the storage unit 520. In the correlation unit 505, when it is determined that association has not been completed for all of the microparticles (Step S80; NO), the process returns to Step S40. In the correlation unit 505, when it is determined that association has been completed for all of the microparticles (Step S80; YES), the process advances to Step S90.

Next, the state determination unit 506 and the evaluation unit 507 determine and evaluate a state of a particle on the basis of the particle correlation list LS2 generated in Step S70. Specific examples of determination of a state of a particle by the state determination unit 506 and evaluation by the evaluation unit 507 will be described below.

Evaluation Example (Part 1): Comparisons Before and after Action of Substance

The evaluation unit 507 can compare and evaluate distributions of the particle size and the zeta potential before a substance acts on microparticles and distributions of the particle size and the zeta potential after a substance acts on microparticles. As a specific example, when a microparticle is an exosome derived from human fibroblastoma, the evaluation unit 507 evaluates distributions of the particle size and the zeta potential when an anti-CD81 antibody acts on the exosome. In this specific example, the correlation unit 505 associates the exosome before the anti-CD81 antibody acts with the zeta potential $\zeta$ and the particle size d and generates a particle correlation list LS2-1. Next, the correlation unit 505 associates the exosome after the anti-CD81 antibody acts with the zeta potential $\zeta$ and the particle size d and generates a particle correlation list LS2-2. As shown in FIG. 15, the evaluation unit 507 outputs the distributions of the particle size and the zeta potential on the basis of the particle correlation list LS2-1 regarding the exosome before the anti-CD81 antibody acts and the particle correlation list LS2-2 regarding the exosome after the anti-CD81 antibody acts.

Figure 16:
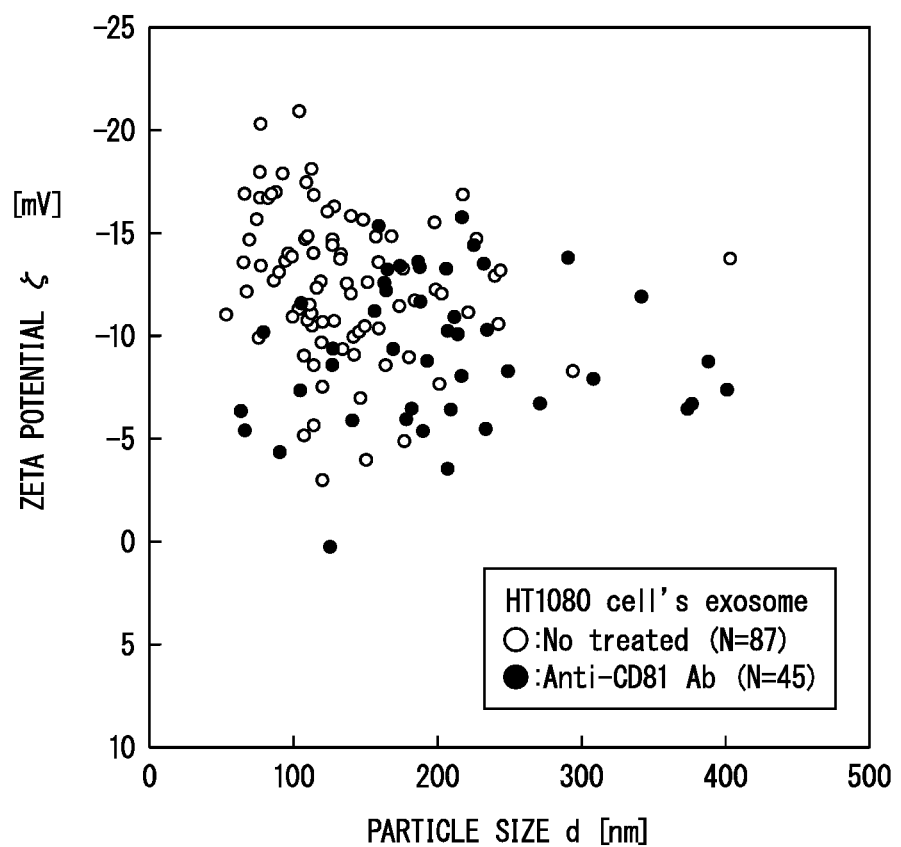
FIG. 16 is a diagram showing an example of distributions of a particle size and a zeta potential output from an evaluation unit of the present embodiment.

FIG. 16 is a diagram showing an example of distributions of the particle size and the zeta potential output from the evaluation unit 507 of the present embodiment. As shown in FIG. 16, the evaluation unit 507 outputs the distributions of the particle size and the zeta potential before the anti-CD81 antibody acts on the exosome and the distributions of the particle size and the zeta potential after the anti-CD81 antibody acts on the exosome. Therefore, the particle detection system 1 can present a change in the distributions of the particle size and the zeta potential when a substance acts on the microparticle.

Evaluation Example (Part 2): Calculation of Threshold Value for Evaluation (Reference Range Information)

The threshold values for evaluating the particle size and the zeta potential that are predetermined have been described above. The evaluation unit 507 may calculate a threshold value for evaluation on the basis of the state of the microparticle. As a specific example, a case in which the evaluation unit 507 calculates a threshold value for evaluation on the basis of the state of the exosome before a substance acts and evaluates the exosome after the substance acts on the basis of the calculated threshold value will be described with reference to FIG. 17 to FIG. 19.

Figure 17:
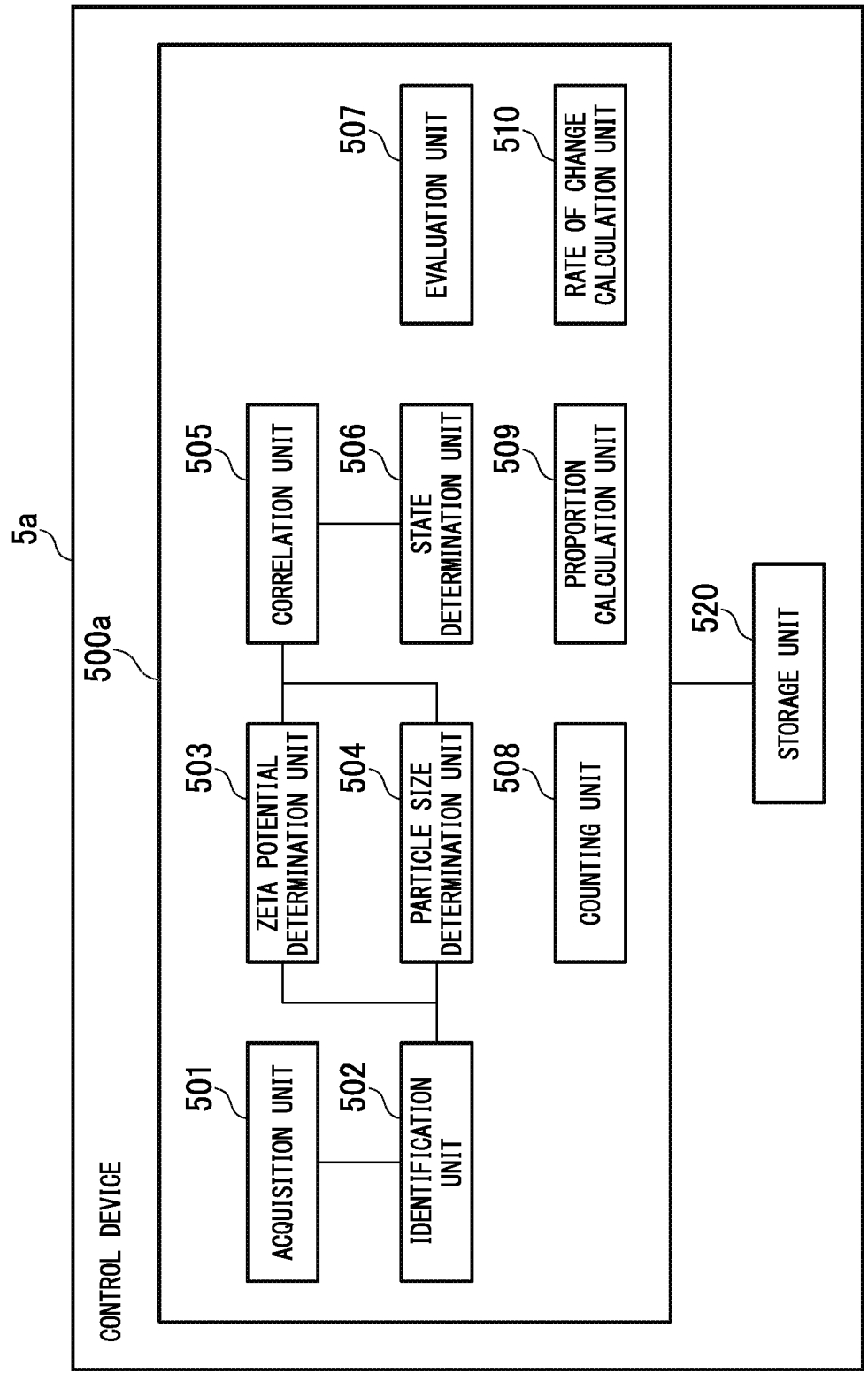
FIG. 17 is a configuration diagram showing an example of a configuration of a control device of the present embodiment.

FIG. 17 is a configuration diagram showing an example of a configuration of a control device 5a of the present embodiment. The control device 5a includes a counting unit 508, a proportion calculation unit 509, and a rate of change calculation unit 510 in addition to functional units included in the operation unit 500 of the control device 5.

For areas separated off using the threshold value Thd of the particle size and the threshold value Thζ of the zeta potential indicated by the reference range information, the counting unit 508 counts the number of the extracellular endoplasmic reticulum included in the area. Here, as examples of the area, there are the area DM1 to the area DM4 described with reference to FIG. 14.

The proportion calculation unit 509 calculates a proportion of the number of pieces of the extracellular endoplasmic reticulum counted by the counting unit 508 in the areas. Specifically, when the number of pieces of the extracellular endoplasmic reticulum counted by the counting unit 508 is set as 100%, the proportion calculation unit 509 calculates a proportion of the number of pieces of the extracellular endoplasmic reticulum in each of the areas for each area.

The rate of change calculation unit 510 calculates a rate of change between the proportion of the extracellular endoplasmic reticulum before the substance acts and the proportion of the extracellular endoplasmic reticulum after the substance acts for each area. For example, the rate of change calculation unit 510 calculates a rate of change between the proportion for each area of the exosome before the anti-CD81 antibody acts and the proportion for each area of the exosome after the anti-CD81 antibody acts for each area.

Figure 18:
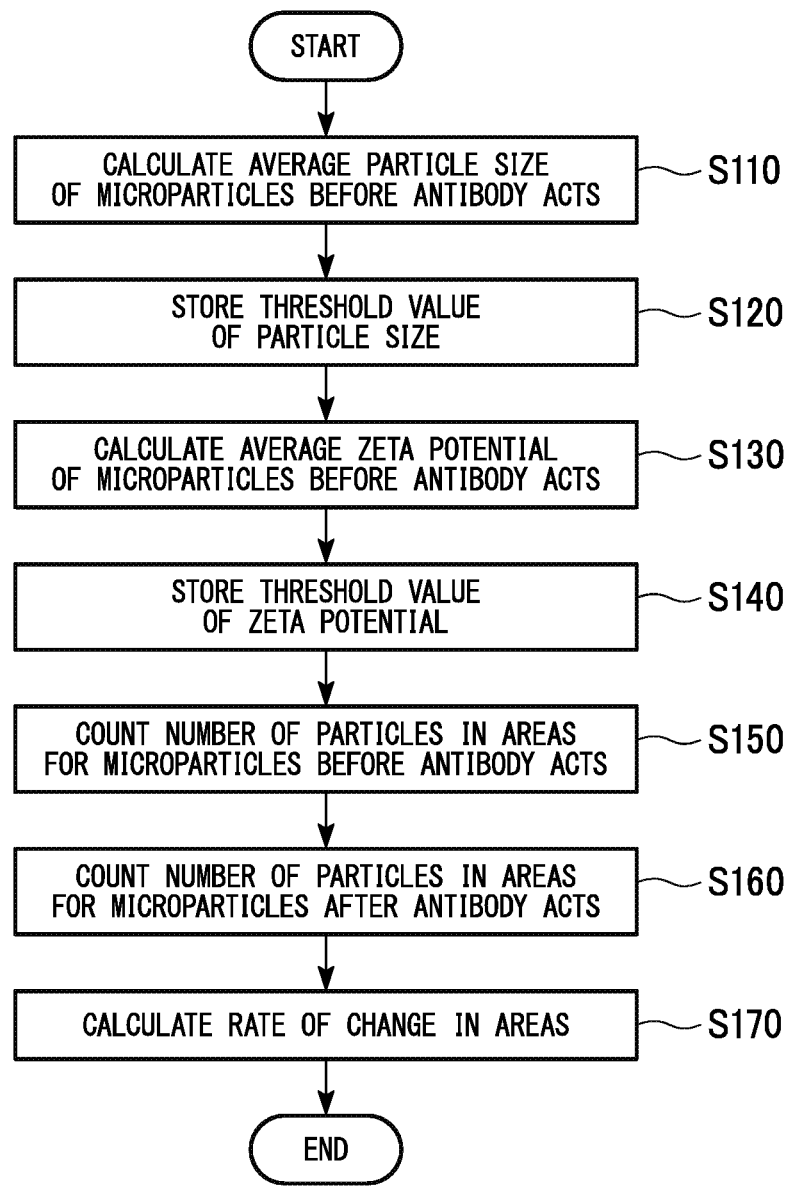
FIG. 18 is a diagram showing a modified example of operations of the control device of the present embodiment.
Figures 19, 20:
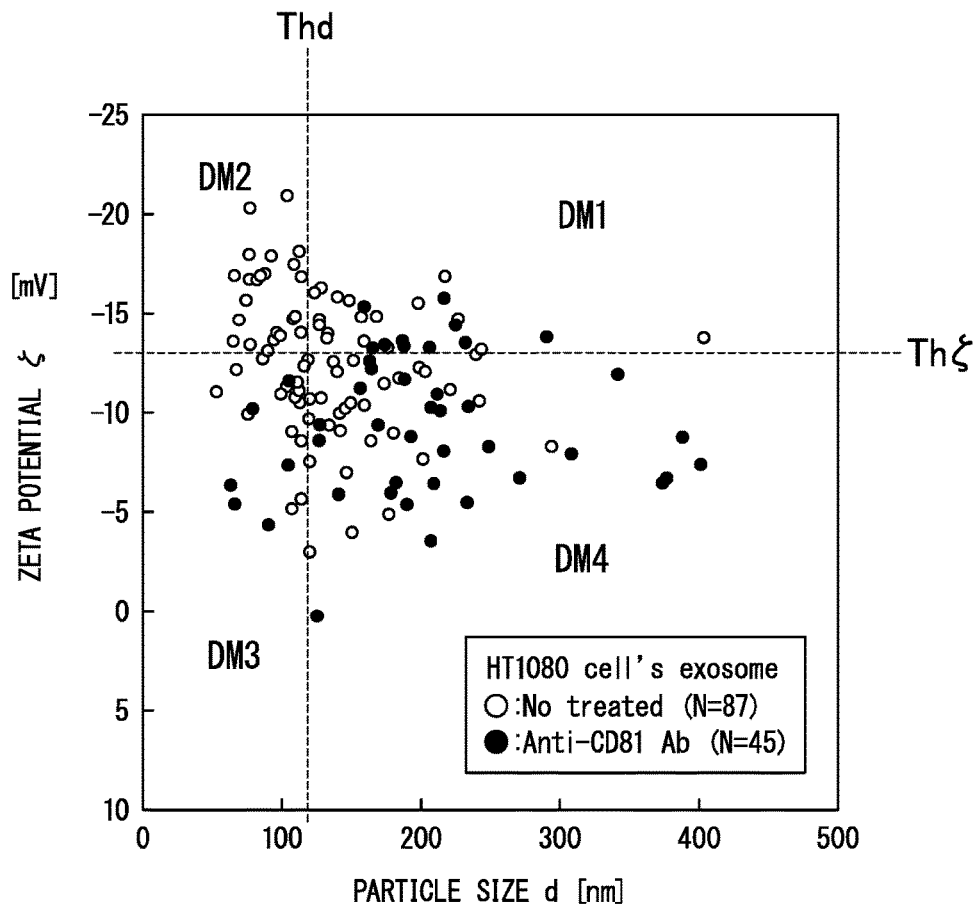
FIG. 19 is a diagram showing an example of threshold values and areas of the present embodiment.
FIG. 20 is a table showing an example of counting results obtained by a counting unit of the present embodiment.

Next, an example of operations of the control device 5a will be described. FIG. 18 is a diagram showing a modified example of operations of the control device of the present embodiment. FIG. 19 is a diagram showing an example of threshold values and areas of the present embodiment.

The particle size determination unit 504 determines the particle size d of the exosome before an antibody acts. The evaluation unit 507 calculates an average value of the particle sizes d determined by the particle size determination unit 504 (Step S110). In this example, the evaluation unit 507 calculates the average particle size as 120 nm. The evaluation unit 507 stores the calculated average particle size 120 nm in the storage unit 520 as the threshold value Thd of the particle size (Step S120). FIG. 19 shows an example of the threshold value Thd calculated by the evaluation unit 507.

The zeta potential determination unit 503 determines the zeta potential of the exosome before the antibody acts. The evaluation unit 507 calculates an average value of the zeta potentials determined by the zeta potential determination unit 503 (step S130). In this example, the evaluation unit 507 calculates the average zeta potential as −(negative) 13 mV. The evaluation unit 507 stores the calculated average zeta potential −13 mV in the storage unit 520 as the threshold value Thζ of the particle size (Step S140). FIG. 19 shows an example of the threshold value Thζ calculated by the evaluation unit 507.

According to the process of Step S110 to Step S140, the threshold values are stored in the storage unit 520.

Next, the counting unit 508 counts the number of particles for each area of the exosome before the antibody acts (Step S150). FIG. 20 shows an example of the counting results obtained by the counting unit 508.

FIG. 20 is a table showing an example of counting results obtained by the counting unit 508 of the present embodiment. Specifically, the counting unit 508 counts the number of particles in the area DM1 to the area DM4 regarding the exosome before the antibody acts as 24, 28, 16, and 19, respectively.

Next, the proportion calculation unit 509 calculates the proportion of the number of particles in the areas on the basis of the number of particles of the exosome counted by the counting unit 508. Specifically, as shown in FIG. 20, the proportion calculation unit 509 calculates the proportion of the number of particles in the area DM1 to the area DM4 as 28%, 31%, 19%, and 22%, respectively.

Next, the counting unit 508 counts the number of particles for each area of the exosome after the antibody acts (Step S160). Specifically, the counting unit 508 counts the number of particles in the area DM1 to the area DM4 regarding the exosome after the antibody acts as 13, 0, 6, and 26, respectively.

Next, the proportion calculation unit 509 calculates the proportion of the number of particles in the areas on the basis of the number of particles of the exosome counted by the counting unit 508. Specifically, as shown in FIG. 20, the proportion calculation unit 509 calculates the proportion of the number of particles in the area DM1 to the area DM4 as 29%, 0%, 13%, and 58%, respectively.

Next, the rate of change calculation unit 510 calculates a rate of change between the proportion calculated in Step S150 and the proportion calculated in Step S160 (Step S170). Specifically, as shown in FIG. 20, the rate of change calculation unit 510 calculates the rate of change of the area DM1 to the area DM4 as +3.5%, −100%, −32%, and +163%, respectively.

The evaluation unit 507 compares the calculated rate of change with a trend of the rate of change that is obtained in advance and thus evaluates the state of the microparticle.

Also, here, while the evaluation unit 507 calculates the threshold value Thd of the particle size on the basis of the average value of the particle size and calculates the threshold value Thζ of the zeta potential on the basis of the average value of the zeta potential, the present invention is not limited thereto. The evaluation unit 507 may calculate a line segment parallel to the axis representing the particle size selected between the maximum value and the minimum value of the particle size distribution as the threshold value Thd of the particle size. In addition, the evaluation unit 507 may calculate a line segment parallel to the axis representing the zeta potential selected between the maximum value and the minimum value of the zeta potential distribution as the threshold value Thζ of the zeta potential.

Evaluation Example (Part 3): Evaluation Based on Factors of Increase and Decrease in Areas The evaluation unit 507 may evaluate the state of the microparticle on the basis of the following trends with respect to the increase and decrease in the number of particles in areas before and after the antibody acts. That is, regarding the area DM1, factors increasing the number of particles include the occurrence of aggregation and factors decreasing thereof include antibody binding and the occurrence of aggregation. In addition, regarding the area DM2, factors increasing the number of particles include deaggregation and factors decreasing thereof include antibody binding and the occurrence of aggregation. In addition, regarding the area DM3, factors increasing the number of particles include antibody binding and factors decreasing thereof include the occurrence of aggregation. In addition, regarding the area DM4, factors increasing the number of particles include antibody binding and the occurrence of aggregation, and factors decreasing thereof include deaggregation.

In addition, the evaluation unit 507 may evaluate the state of the microparticle on the basis of the following trends with respect to the increase and decrease in the number of particles in areas predicted by antibody binding. That is, regarding the area DM1, as a result of the antibody action, the particles move to the area DM4. In this case, the mechanism envisaged is antibody binding. In addition, regarding the area DM2, as a result of the antibody action, the number of particles decreases. In this case, the mechanism envisaged includes antibody binding and the occurrence of aggregation. In addition, regarding the area DM3, as a result of the antibody action, the particles move to the area DM4. In this case, the mechanism envisaged includes antibody binding and the occurrence of aggregation. In addition, regarding the area DM4, as a result of the antibody action, the number of particles increases.

In this case, the mechanism envisaged includes antibody binding and the occurrence of aggregation.

In this example, the threshold value indicating the above trends is stored in the storage unit 520 as the threshold value of the rate of change. The evaluation unit 507 compares the increase and decrease rate calculated in the procedures shown in FIG. 18 to FIG. 20 with the threshold value of the rate of change stored in the storage unit 520 and thus evaluates the state of the microparticle.

Evaluation Example (Part 4): Evaluation by Reacting Antibodies of Different Types for Each Flow Path In addition, since the particle detection system 1 includes a plurality of lanes, it is possible to change the type of the microparticle and the type of the antibody for each lane. Specific examples are shown in FIG. 21 to FIG. 23.

Figure 21:
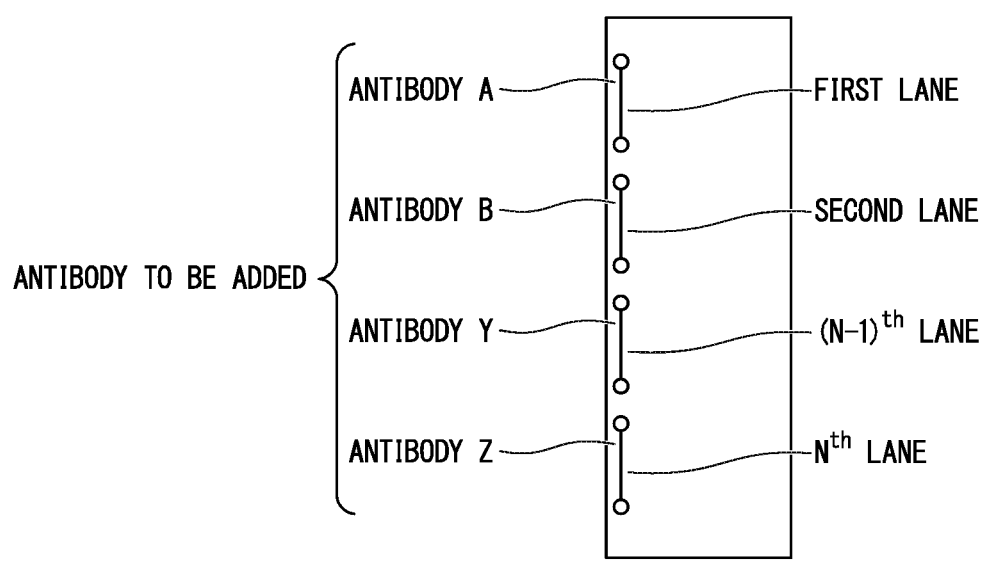
FIG. 21 is a schematic diagram showing an example in which antibodies of different types are added to a plurality of lanes of the present embodiment.

FIG. 21 is a schematic diagram showing an example in which antibodies of different types are added to a plurality of lanes of the present embodiment.

FIG. 22 is a table showing an example of a disease determination panel of the present embodiment.

FIG. 23 is a table showing an example of diagnosis and an instruction panel of diseases of the present embodiment.

As shown in FIG. 21 to FIG. 23, the evaluation unit 507 can add different antibodies for each lane and evaluate the state of the microparticle in each lane. That is, according to the particle detection system 1, it is possible to arbitrarily select a combination of antibodies optimal for diagnosis of a target disease and perform an examination. In addition, according to the particle detection system 1, since it is possible to evaluate a plurality of lanes simultaneously, it is possible to shorten an evaluation time compared to when evaluation is performed by a single lane.

Evaluation Example (Part 5): Evaluation of Physical Properties of Functionally Modified Exosome The evaluation unit 507 can evaluate physical properties of the microparticle. As a specific example, a case in which the evaluation unit 507 evaluates physical properties of a functionally modified exosome will be described with reference to FIG. 24 to FIG. 26.

Figure 24:
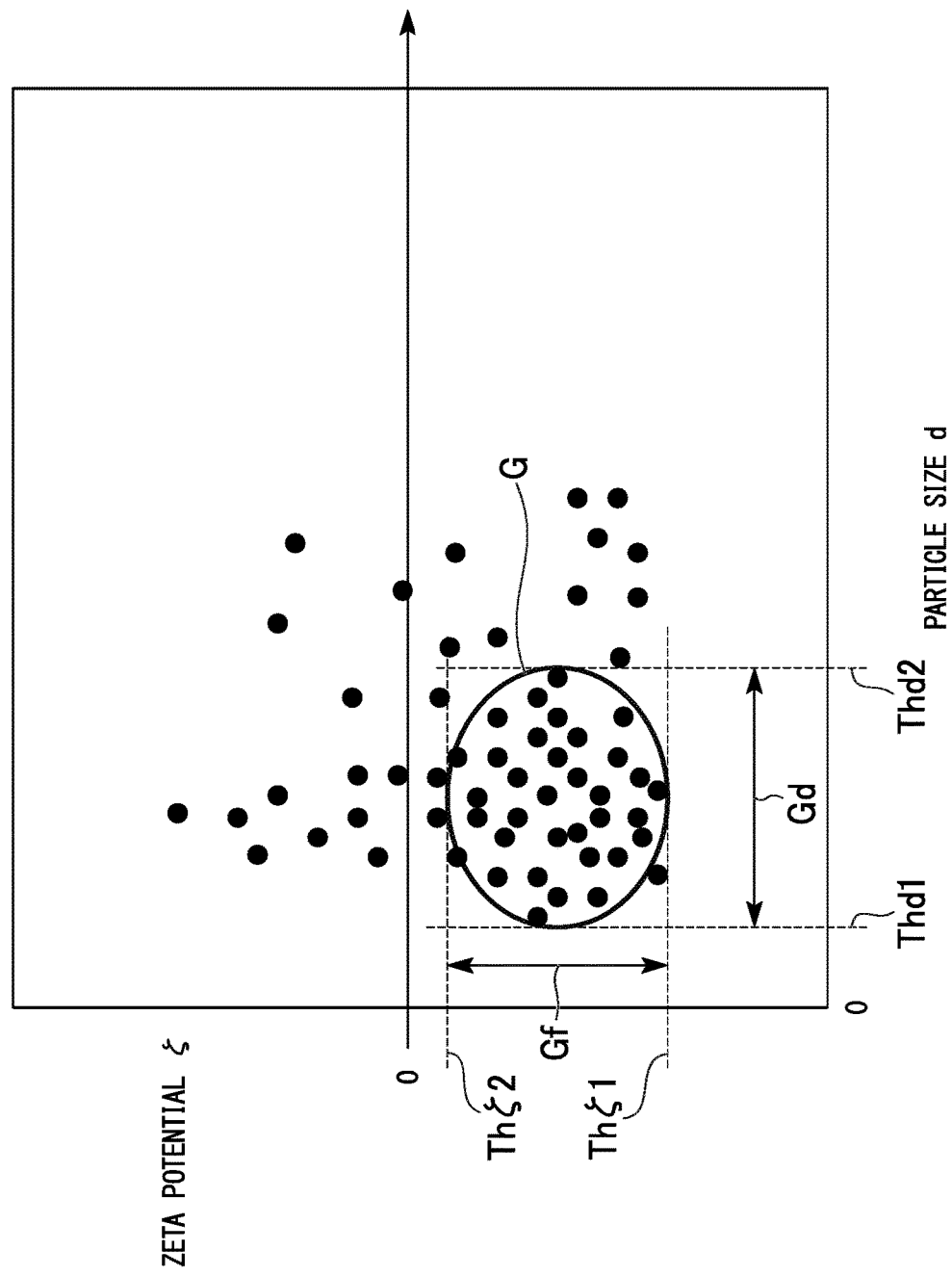
FIG. 24 is a diagram showing an example of a gate area of the present embodiment.

FIG. 24 is a diagram showing an example of a gate area G of the present embodiment. Here, the gate area G is an area surrounded by a lower limit threshold value Thd1 and an upper limit threshold value Thd2 of the particle size d and a lower limit threshold value $Th\zeta1$ and an upper limit threshold value $Th\zeta2$ of the zeta potential $\zeta$. The evaluation unit 507 of the present embodiment evaluates physical properties of particles using an area between the lower limit threshold value Thd1 of the particle size d and the upper limit threshold value Thd2 of the particle size d as a gate area Gd of the particle size d. In addition, the evaluation unit 507 evaluates physical properties of particles using an area between the lower limit threshold value $Th\zeta1$ of the zeta potential $\zeta$ and the upper limit threshold value $Th\zeta2$ of the zeta potential as gate area G of the zeta potential $\zeta$. While these threshold values that are stored in the storage unit 520 in advance will be described below, the present invention is not limited thereto. These threshold values may be calculated by an operation performed by the operation unit 500 or may be supplied from the outside of the control device 5.

Next, an example of operations of evaluating physical properties of microparticles performed by the operation unit 500 will be described with reference to FIG. 25.

Figure 25:
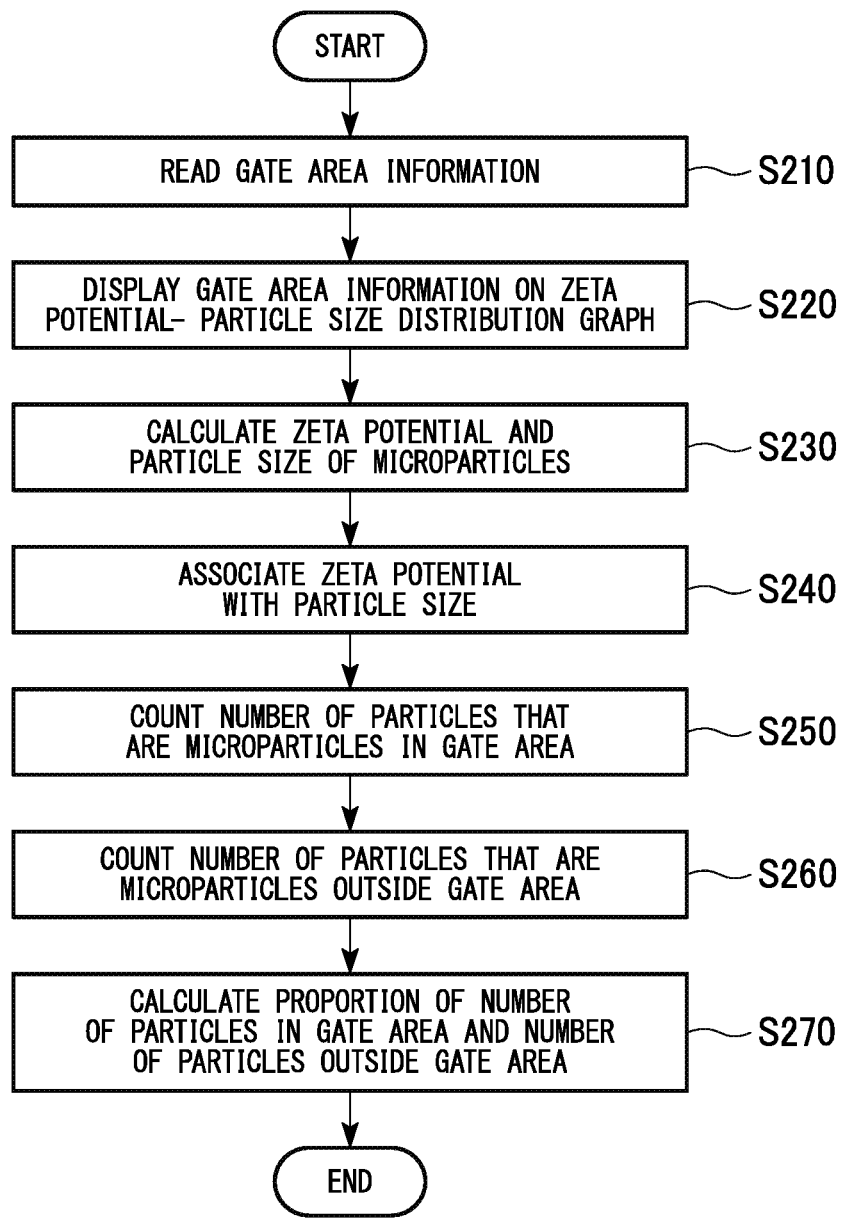
FIG. 25 is a diagram showing an example of operations of evaluating physical properties of microparticles performed by an operation unit of the present embodiment.

FIG. 25 is a diagram showing an example of operations of evaluating physical properties of microparticles performed by the operation unit 500 of the present embodiment.

The evaluation unit 507 reads the lower limit threshold value Thd1 and the upper limit threshold value Thd2 of the particle size d and the lower limit threshold value $Th\zeta1$ and the upper limit threshold value $Th\zeta2$ of the zeta potential $\zeta$ from the storage unit 520 (Step S210).

The evaluation unit 507 displays information indicating the gate area on the basis of the threshold values read in Step S210 on a display (not shown) (refer to the gate area G in FIG. 24) (Step S220).

Next, the zeta potential determination unit 503 determines the zeta potential of an evaluation target microparticle. In addition, the particle size determination unit 504 determines the particle size d of the evaluation target microparticle (Step S230). In this specific example the evaluation target microparticle is a functionally modified exosome.

Next, the correlation unit 505 associates the zeta potential determined in Step S230 with the particle size d for each microparticle (Step S240). In addition, the correlation unit 505 displays the associated zeta potential $\zeta$ and particle size d on a display (not shown) for each microparticle.

The counting unit 508 counts the number of particles of microparticles present in the gate area G (Step S250). In addition, the counting unit 508 counts the number of particles of microparticles outside the gate area G (Step S260).

The proportion calculation unit 509 calculates the proportion of the number of particles in the gate area G and the number of particles outside the gate area G on the basis of the number of particles counted by the counting unit 508 (Step S270), and the process ends.

Next, an example of evaluation performed by the evaluation unit 507 will be described with reference to FIG. 26.

FIG. 26 is a diagram showing an example of evaluation performed by the evaluation unit 507 of the present embodiment. As shown in FIG. 26, when the number of particles present in the gate area G is relatively large, the evaluation unit 507 determines it as suitable, and when the number of particles present in the gate area G is relatively small, the evaluation unit 507 determines it as unsuitable. That is, the evaluation unit 507 determines compatibility of the evaluation target microparticle on the basis of the number of particles in the gate area G and the number of particles outside the gate area G.

Here, a technology for modifying functions of exosomes according to the purpose of treating diseases is known. For example, the exosome can be used as a drug carrier in a drug delivery system. As an example, arbitrary protein genes are introduced into cells using virus vectors using a genetic engineering technique and exosomes are collected from the cells. Accordingly, the exosomes can be used as delivery carriers for siRNA and miRNA. In addition, for example, functionally modified exosomes in which a specific binding substance is bound to exosomes can be prepared and used.

According to the above-described evaluation unit 507, it is possible to evaluate whether functionally modified exosomes are suitable for the above-described drug delivery system.

SUMMARY

As described above, the particle detection system 1 according to the present embodiment obtains the particle size and the zeta potential of the microparticle for each microparticle and correlates the obtained particle size and zeta potential.

Thus, according to the particle detection system 1, it is possible to determine the state of a microparticle which was difficult to determine when only either the particle size or the zeta potential was used.

In addition, the particle detection system 1 according to the present embodiment causes illumination light to be incident from the side surface of the lane 2 so that it is possible to detect scattered light generated from the microparticle with high accuracy. Thus, according to the particle detection system 1, it is possible to determine the particle size and the zeta potential of the microparticle with high accuracy. Thus, according to the particle detection system 1, it is possible to determine the state of the microparticle with high accuracy.

Here, while a configuration in which a force due to an electric field is applied to move particles into the flow path 13 has been exemplified in the above embodiment, the present invention is not limited thereto. For example, a configuration in which particles are moved in a predetermined direction by applying a flow velocity to a medium or a configuration in which a force moving particles in a predetermined direction is not applied may be used.

Here, while a configuration in which scattered light generated from particles toward the −z side is detected has been described in the above embodiment, the present invention is not limited thereto. For example, a configuration in which scattered light scattered toward the +y side, −y side, or +z side is detected may be used. The detection unit may be provided not only on the bottom surface of the flow path, but also provided on the side surface of the flow path. For example, when illumination light is emitted from the side surface of the flow path, side-scattered light may be detected from the bottom surface side of the flow path or side-scattered light may be detected from the upper surface side of the flow path. In addition, a configuration in which forward-scattered light is detected may be used. For example, when illumination light is emitted from the side surface of the flow path, backward-scattered light may be detected from the illumination light exit side of the flow path and forward-scattered light may be detected from the illumination light exit side of the flow path.

Here, while the fluid device C including the plurality of lanes 2 arranged in the length direction (y direction) has been exemplified in the above embodiment, the plurality of lanes 2 may be arranged in the height direction (z direction). In this case, the solution may be injected in the length direction (x direction) or may be injected in the y direction. For example, there may be a plurality of emission light sources, and the light sources may emit light to microparticles that flow in the lanes 2 with corresponding heights. In addition, a direction in which light is emitted from at least one emission light source may be changed and thus light may be emitted to microparticles that flow in the lane 2.

Here, in order to adjust a position at which the width of the illumination light L1 in the z direction has the minimum size, for example, a configuration in which, as a second adjustment unit, a plurality of adjustment units CL (lenses) having different focal lengths are provided on a turret plate, the turret plate is rotated, and a lens having a desired focal length is positioned on the optical path of the illumination light L1, or a configuration using a zoom lens can be used. In addition, a configuration in which a plurality of adjustment units CL having different effective diameters are used, a lens having a desired effective diameter is positioned on the optical path of the illumination light L1, and an adjustable NA diaphragm is used to change an effective diameter of a condenser lens may be used. Further, a configuration in which a plurality of expander lenses 22 having different magnifications are used, and the expander lens 22 having a desired effective diameter is positioned on the optical path of the illumination light L1 or a configuration in which a component using a zoom lens is used to change the magnification may be used.

Here, while a configuration in which the optical axis of the illumination light L1 is parallel to the x axis has been exemplified, the present invention is not limited thereto. For example, the optical axis may be tilted by ±10 degrees or ±5 degrees with respect to the x axis as long as it is in the range intersecting the above-described orthogonal plane. When the optical axis of the illumination light L1 is parallel to the x axis and enters orthogonally to the side surface 16a, the scattering angle dependence of Rayleigh scattered light becomes the weakest in principle. However, as described above, when Mie scattered light from particles larger than measurement target particles is cut, noise is reduced, and when the optical axis of the illumination light L1 is inclined with respect to the x axis, there is a possibility of the signal strength of Rayleigh scattered light increasing.

Here, while a configuration in which exosomes are used as particles has been exemplified in the above embodiment, it should be noted that the present device and the present system can be applied to particles other than an exosome. For example, the present device and the present system can be broadly applied to not only organic particles represented by autologous cell derived particles such as exosomes (extracellular endoplasmic reticulum) and foreign particles such as bacteria and viruses but also inorganic particles such as a metal and silica.

Here, a case in which the particle detection system 1 determines the state of the microparticle and identifies the type of the microparticle has been exemplified in the above embodiment. Here, the state of the microparticle determined by the particle detection system 1 includes aggregation of microparticles, a binding state between the microparticle and the antibody, and the like. In addition, the type of the microparticle identified by the particle detection system 1 includes an exosome, a microvesicle, an apoptotic substance, a cell, a polymer micelle, and the like.

Since the particle detection device 100 detects side-scattered light generated from the particle, image information with less noise is obtained compared to when forward-scattered light is received. In addition, for example, regarding the illumination light L1, when a passage area of the emission light flux at a position on the side surface 16a is not confined within the side surface 16a, and a part K of the illumination light L1 enters the inside of the flow path 13 through the bottom plate 11, scattered light may be generated on the side surface 16*b* or the bottom surface 16*c*. The signal strength of scattered light generated on the side surface 16*b* or the bottom surface 16*c* is several orders or more in magnitude greater than the signal strength of scattered light generated from the observation target particle and exceeds a dynamic range of the imaging unit 32. While particles are observed, scattered light generated from the side surface 16*b* or the bottom surface 16*c* (hereinafter referred to as a wall surface) may saturate the imaging unit 32. Then, when the scattered light is generated from a wide range in the z direction, due to spreading according to defocusing, scattered light greatly erodes the observation area in the flow path on the imaging unit 32. In the present embodiment, since the illumination light L1 converges so that a passage area of the illumination light L1 at a position on the side surface 16*a* is confined within the side surface 16*a* and a passage area of the illumination light L1 at a position on the end surface 17 is confined within the end surface 17, it is possible to prevent the generation of scattered light having a large signal strength. Therefore, the particle detection device 100 can detect information about particles in the flow path 13 with high accuracy.

In addition, scattered light from particles outside the depth of focus DOF of the detection unit 30 becomes background light due to defocusing and cannot be detected in the form of particles. In the present embodiment, since the width in the z direction becomes a minimum inside the flow path 13 and background light outside the observation area in the flow path 13 is minimized, it is possible to detect particles illuminated with the illumination light L1 with high accuracy. In addition, in the present embodiment, since the end surface 17 is mirror-finished, it is possible to prevent scattered light from becoming noise on the end surface 17 and adversely influencing particle detection accuracy. In addition, in the present embodiment, since the illumination light L1 is incident orthogonally to the end surface 17, the optical axis is adjusted easily. Further, in the present embodiment, since the end surface 19 of the bottom plate 11 is separated from the incident side of the illumination light L1 on the opposite side to the end surface 17 of the reservoir member 10, it is possible to prevent some of the illumination light L1 from entering the end surface 19 before it enters the end surface 17.

Here, while a case in which microparticles are moved in a predetermined direction by electrophoresis has been described in the particle detection device 100 according to the above-described embodiment, the present invention is not limited thereto. For example, the particle detection device 100 may move microparticles in a predetermined direction by applying a flow velocity to the medium. In addition, the particle detection device 100 may have a configuration in which a force moving microparticles in a predetermined direction is not applied.

In addition, while a case in which the particle detection device 100 and the control device 5 are separate devices has been described in the above-described embodiment, the present invention is not limited thereto. In the particle detection system 1, the particle detection device 100 and the control device 5 may be an integrated device. For example, in the particle detection system 1, the control device 5 may be configured as a computer incorporated into the particle detection device 100. In such a configuration, the particle detection system 1 can reduce the size and mounting area of the device compared to when separate devices are provided.

Here, some functions of the particle detection device 100 in the above-described embodiment may be realized by a computer. In this case, a program for realizing this control function is recorded in a computer readable recording medium, and a computer system reads and executes the program recorded in the recording medium for realization. Note that the "computer system" here is a computer system built into the particle detection device 100 and includes an OS and hardware such as peripheral devices. In addition, the "computer readable recording medium" refers to a portable medium such as a flexible disk, a magneto optical disc, a ROM, and a CD-ROM and a storage device such as a hard disk built into the computer system. Further, the "computer readable recording medium" may include a medium that dynamically maintains a program for a short time like a communication line when a program is transmitted via a network such as the Internet or a communication line such as a telephone line and a medium that maintains a program for a certain time like a volatile memory in the computer system serving as a server or a client in that case. In addition, the program may be a program for realizing some of the above-described functions and the above-described functions may be realized in a combination with a program already recorded in the computer system. In addition, some or all of the functional blocks of the particle detection device 100 in the above-described embodiment may be realized by an integrated circuit such as a large-scale integration (LSI) circuit. The functional blocks of the particle detection device 100 may be individually implemented as a processor or some or all thereof may be integrally implemented as a processor. In addition, a method of forming an integrated circuit is not limited to an LSI circuit, and may be realized by a dedicated circuit or a general-purpose processor.

In addition, if an integrated circuit technology that replaces an LSI circuit emerges according to progress in semiconductor technology, an integrated circuit according to this technology may be used.

While exemplary embodiments according to the present invention have been described above with reference to the accompanying drawings, it should be noted that the present invention is not limited to such examples. The forms and combinations of the constituent members shown in the above-described examples are only examples, and various modifications can be made based on design requirements or the like without departing from the spirit and scope of the present invention.

The invention claimed is:
1. A microparticle detection system, comprising:
a stage having a fluid device mounting surface;
a particle size measurer to determine a particle size of microparticles that move in a flow path of a fluid device mounted on the fluid device mounting surface;
a zeta potential measurer to determine a zeta potential of the microparticles that move in the flow path of the fluid device mounted on the fluid device mounting surface;
a particle size and zeta potential correlator to associate the particle size for each of the microparticles determined by the particle size measurer with the zeta potential for each of the microparticles determined by the zeta potential measurer for each of the microparticles; and
a microparticle identifier to identify the microparticles,
wherein the particle size measurer and the zeta potential measurer determine the particle size and the zeta potential for each of the microparticles identified by the microparticle identifier.

2. The microparticle detection system according to claim 1, further comprising
- a light emitter to emit illumination light to the flow path; and
- an imager to image scattered light generated when the illumination light is emitted;
- wherein the microparticle identifier is configured to identify the microparticles included in the image for each of the microparticles on the basis of the image captured by the imager.

3. The microparticle detection system according to claim 2, further comprising
- memory to store reference range information indicating a reference range of the particle size and a reference range of the zeta potential, and
- a state determiner to determine at least one of a type and a state of the microparticle on the basis of correlation information obtained by the particle size and zeta potential correlator associating the particle size with the zeta potential for each of the microparticles and the reference range information stored in the memory.

4. The microparticle detection system according to claim 3,
- wherein, at least one area separated off using the reference range of the particle size and the reference range of the zeta potential indicated by the reference range information, the state determiner determines at least one of the type and the state of the microparticle included in the area.

5. The microparticle detection system according to claim 3,
- wherein the state determiner outputs distributions of the particle size and the zeta potential for each of the microparticles for the plurality of microparticles.

6. The microparticle detection system according to claim 4, further comprising
- a counter to count a number of the microparticles included in the area for areas separated off using a threshold value of the particle size and a threshold value of the zeta potential indicated by the reference range information.

7. The microparticle detection system according to claim 3,
- wherein the microparticle includes a complex in which a biological molecule on a surface is bound to another substance, and
- wherein the state determiner identifies a type of the complex on the basis of the correlation information and the reference range information.

8. The microparticle detection system according to claim 7,
- wherein the microparticle is an exosome, and
- wherein the state determiner detects a specific binding substance that specifically binds to a surface of the exosome on the basis of the identified type of the complex.

9. The microparticle detection system according to claim 3, further comprising
- an evaluator to evaluate distributions of at least one of the type and the state of the microparticle on the basis of determination by the state determiner.

10. The microparticle detection system according to claim 4,
- wherein the reference range information is stored in advance for each of the distributions of the state of the microparticle used for determination by the state determiner.

11. The microparticle detection system according to claim 3,
- wherein the reference range information is determined on the basis of the distributions of the particle size and the zeta potential of the plurality of microparticles of which no substance is bound to a biological molecule on a surface.

12. The microparticle detection system according to claim 5, further comprising
- a proportion calculator to calculate a proportion between the areas of a number of the microparticles counted by the counter, and
- a rate of change calculator to calculate a rate of change between a proportion of a number of the microparticles between the areas that is calculated by the proportion calculator for the microparticles before reacting with a certain substance and a proportion of a number of the microparticles between the areas that is calculated by the proportion calculator for the microparticles after reacting with the substance.

13. The microparticle detection system according to claim 3,
- wherein the particle size measurer determines the particle size on the basis of Brownian motion of the microparticle identified by the microparticle identifier.

14. The microparticle detection system according to claim 3,
- wherein the zeta potential measurer determines the zeta potential on the basis of a movement speed of the microparticle identified by the microparticle identifier.

15. The microparticle detection system according to claim 3,
- wherein the light emitter emits illumination light to the flow path along an optical axis that is orthogonal to the fluid device mounting surface and parallel to a first direction intersecting a plane parallel to the flow path,
- the microparticle detection system further comprising
- a light adjuster to converge the illumination light so that a width of the illumination light in a second direction orthogonal to the first direction becomes a minimum inside the flow path and an emission area at a position on a side surface on an emission light incident side of the flow path is confined within the side surface.

16. The microparticle detection system according to claim 3,
- wherein the microparticle is an exosome or an extracellular endoplasmic reticulum to which another substance is not bound or bound.

17. The microparticle detection system according to claim 2,
- wherein the microparticle identifier assigns a unique microparticle identifier for each of the identified microparticles, and
- wherein the particle size and zeta potential correlator associates the particle size for each of the microparticles with the zeta potential for each of the microparticles determined by the zeta potential measurer for each of the microparticles on the basis of matching between the microparticle identifier assigned to the microparticle of which the particle size is determined by the particle size measurer and the microparticle identifier assigned to the microparticle of which the zeta potential is determined by the zeta potential measurer.

18. A non-transitory computer readable medium storing a microparticle detection program, the program causing a computer including a stage having a fluid device mounting surface to execute:
- determining a particle size of microparticles that move in a flow path of a fluid device mounted on the fluid device mounting surface;
- determining a zeta potential of the microparticles that move in the flow path of the fluid device mounted on the fluid device mounting surface;
- associating the particle size with the zeta potential of the microparticle for each of the microparticles;
- displaying an area separated off on the basis of a threshold value of the particle size and a threshold value of the zeta potential;
- displaying distributions of the particle size and the zeta potential for each of the microparticles; and
- identifying the microparticles,
- wherein, in determining the particle size and determining the zeta potential, the particle size and the zeta potential are determined for each of the microparticles identified in the identifying.

19. The non-transitory computer readable medium storing the microparticle detection program according to claim 18, the program causing the computer to further execute
- counting a number of the microparticles included in a specific area among areas separated off using a threshold value of the particle size and a threshold value of the zeta potential.

20. The non-transitory computer readable medium storing the microparticle detection program according to claim 19, the program causing the computer to further execute
- emitting illumination light to the flow path; and
- imaging scattered light generated when the illumination light is emitted;
- wherein the identifying identifies the microparticles included in the image for each of the microparticles on the basis of the image captured in the imaging.

21. The non-transitory computer readable medium storing the microparticle detection program according to claim 20,
- wherein the emitting comprises emitting illumination light the flow path along an optical axis that is orthogonal to the fluid device mounting surface and parallel to a first direction intersecting a plane parallel to the flow path, and
- the illumination light is adjusted so that a width of the illumination light in a second direction orthogonal to the first direction becomes a minimum inside the flow path and an emission area at a position on a side surface on an emission light incident side of the flow path is confined within the side surface.

* * * * *